United States Patent [19]

Hamper et al.

[11] Patent Number: 5,668,088
[45] Date of Patent: Sep. 16, 1997

[54] HERBICIDAL SUBSTITUTED 3-ARYL-PYRAZOLES

[75] Inventors: Bruce C. Hamper, Kirkwood; Lisa L. Mc Dermott, Sullivan, both of Mo.

[73] Assignee: Monsanto Company, St. Louis, Mo.

[21] Appl. No.: 476,518

[22] Filed: Jun. 7, 1995

[51] Int. Cl.$^6$ .......................... A01N 43/56; C07D 231/12
[52] U.S. Cl. .................. 504/280; 548/375.1; 548/376.1; 548/377.1
[58] Field of Search .................... 548/375.1, 376.1, 548/377.1; 504/280

[56] References Cited

U.S. PATENT DOCUMENTS 5,281,571  1/1994  Woodard et al. ................. 504/225

OTHER PUBLICATIONS

Miura et al I, "Preparation of 3—or 5—, etc" CA 114:164226b (1991).
Miura et al II, "Preparation of 3—or 5—, etc." CA 115:92260d (1991).
Grimmett, et al., "Synthesis and Reactions of Lithiated Monocyclic Azoles Containing Two or More Hetero–Atoms. Part III: Pyrazoles," *Heterocycles* (1994), vol. 37, No. 3, pp. 2067–2147.
Hojo, et al., "A Useful One–Step Synthesis of β–Trihaloacetylvinyl Ethers and Trihaloacetylketene Acetals," *Synthesis Communications* (1986), pp. 1013–1014.
Kamitori, et al., "A New Convenient Synthetic Method for 3–Allyl–1,1,1–trifluoroacetylacetone and its Derivatives," *Synthesis Communications* (1986), pp. 340–342.

*Primary Examiner*—Patricia L. Morris
*Attorney, Agent, or Firm*—Grace L. Bonner; Arnold, White & Durkee

[57] ABSTRACT

The invention herein relates to certain substituted-arylpyrazole compounds, herbicidal compositions containing same, herbicidal methods of use and processes for preparing said compounds.

12 Claims, No Drawings

HERBICIDAL SUBSTITUTED 3-ARYL-PYRAZOLES

FIELD OF THE INVENTION

The field of the invention contemplated herein pertains to herbicidal compounds generically defined by the above title, to compositions containing same and processes for preparing said compounds.

BACKGROUND OF THE INVENTION

Various substituted 3-aryl-pyrazole type compounds are known in the literature. Such compounds have various utilities, e.g., as chemical intermediates, pharmaceuticals and herbicides.

Among the substituted 3-aryl-5-(halo) alkyl-pyrazoles in the art are those having a variety of substituent radicals on the aryl and/or pyrazole moieties of the compound, e.g., alkyl, carboxyl, alkoxycarbonyl, formyl, phenyl and phenyl substituted with various groups such as alkyl, halo or nitro groups, etc. For example, compounds of this type are known wherein the aryl moiety is a substituted or unsubstituted phenyl radical, in which the substituent radicals are alkyl, cycloalkyl, alkaryl, halogen, trifluoromethyl, etc., and the pyrazolyl radical is substituted in various positions on the nitrogen or carbon atoms with alkyl, halogen, alkoxy, hetero-cycles, $S(O)_n R$ members, wherein n is 0–2 and R may be a variety of radicals such as those substituted on the aryl or pyrazole moieties.

Compounds of the above type having utility as herbicides, typically require application rates as high as five or ten or more kilograms per hectare to achieve adequate weed control. For example, Japanese patent application No. 1-225724 by Miura et al. discloses a number of 3-phenyl pyrazole derivatives most of which required a dose of 5 kg/hectare for adequate weed control in both pre-emergent and post emergent tests. In particular, 3-phenyl pyrazole derivatives having alkyl or haloalkyl substitutions in the 4 position of the pyrazole ring were disclosed and exemplified by two compounds having 4-methyl substitutions and in the 5 position either —$SCH_3$ (compound 360) or —$SOCH_3$ (compound 570). Only one of these, compound No. 360, was tested for weed control and a dose of 5 kg/hectare was required for effective post-emergent weed control. At 0.8 Kg/hectare, weed control was ineffective.

Thus, in accordance with the present invention, it has been discovered that a novel class of 4-substituted alkyl and haloalkyl arylpyrazole-type compounds have uniquely and surprisingly high phytotoxic unit activity against a spectrum of weeds, including narrow-leaf and broadleaf weeds yet maintain a high degree of safety in a plurality of crops, especially small grains and/or row crops such as wheat, barley, corn, soybeans, peanuts, etc.

The 1-(halo)alkyl-3-(substituted)aryl-4-(halo)alkyl-5-haloalkylpyrazoles described herein are new.

SUMMARY OF THE INVENTION

This invention relates to herbicidally-active compounds, compositions containing these compounds, processes for making them and herbicidal methods of using the same.

The herbicidal compounds of this invention are characterized by the structure of Formula I

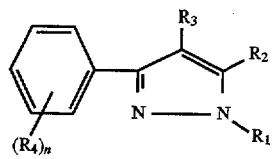

and agriculturally-acceptable salts and hydrates thereof wherein $R_1$ is independently $C_{1-8}$ alkyl; $C_{3-8}$ cycloalkyl, cycloalkenyl, cycloalkylalkyl, or cycloalkenylalkyl; $C_{2-8}$ alkenyl or alkynyl; benzyl; or said $R_1$ members substituted with halogen, amino, nitro, cyano, hydroxy, alkoxy, alkylthio,

$R_2$ is $C_{1-6}$ haloalkyl;
$R_3$ is $C_{1-6}$ alkyl, $C_{1-6}$ haloalkyl, CHO or $CH_2OH$;
$R_4$ members are independently an $R_1$ member, thioalkyl, polyalkoxyalkyl, carbamyl, halogen, amino, nitro, cyano, hydroxy, $C_{3-10}$ heterocycle contain O, $S(O)_m$ and/or $NR_{18}$ hetro atoms, $C_{6-12}$ aryl, aralkyl or alkaryl,

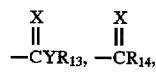

$YR_{15}$, or $NR_{16}R_{17}$ group; or two $R_4$ groups may be combined through a saturated and/or unsaturated carbon, —(C=X)—, or hetero O, $S(O)_m$ and/or $NR_{18}$ linkage to form a cyclic ring having up to 9 ring members which may be substituted with an $R_1$ member, halogen, amino, nitro, cyano, hydroxy, aryl, aralkyl, alkaryl,

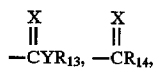

$YR_{15}$ or $NR_{16}R_{17}$;
X is O, $S(O)_m$, $NR_{19}$ or $CR_{20}R_{21}$;
Y is O, $S(O)_m$ or $NR_{22}$;
$R_{8-22}$ are hydrogen, $C_{1-8}$ alkyl, $C_{3-8}$ cycloalkyl, cycloalkenyl, cycloalkylalkyl, or cycloalkenylalkyl, $C_{2-8}$ alkenyl or alkynyl, benzyl, or said $R_1$ members substituted with halogen, amino, nitro, cyano, hydroxy, alkoxy, alkylthio, halogen, amino, nitro, cyano, hydroxy, aryl, aralkyl, alkaryl, carboxyl, alkoxyalkyl, alkylamino, dialkylamino, alkoxy, or carbamyl;
m is 0–2 and
n is 1–5.

A preferred subgenus of the substituted-arylpyrazolyl compounds in this invention are those according to Formula II:

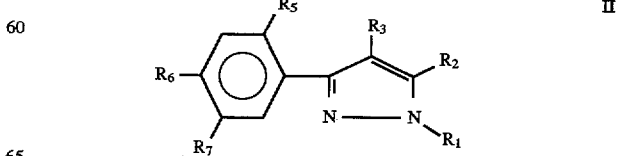

and agriculturally-acceptable salts and hydrates thereof wherein $R_1$ is $C_{1-6}$ alkyl;

$R_2$ is $C_{1-6}$ haloalkyl;

$R_5$ and $R_6$ are independent halogen; and $R_7$ is

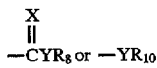

Particularly preferred compounds of this invention are compounds according to Formula II and agricultuarlly-acceptable salts and hydrates thereof wherein $R_1$ is $CH_3$;

$R_2$ is $CF_3$;

$R_3$ is $CH_3$, $CH_2F$ or $CF_2H$;

$R_5$ is F;

$R_6$ is Cl; and $R_7$ is

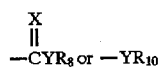

Particularly preferred species of this invention include the following:

2-chloro-5-[1,4-dimethyl-5-(trifluoromethyl)-1H-pyrazol-3-yl]-4-fluorobenzoic acid, 1-methylethyl ester;

2-chloro-5-[1,4-dimethyl-5-(trifluoromethyl)-1H-pyrazol-3-yl]-4-fluorobenzoic acid ethyl ester;

2-chloro-5-[4-(difluoromethyl)-1-methyl-5-(trifluoromethyl)-1H-pyrazol-3-yl]-4-fluorobenzoic acid, 1-methylethyl ester; and 2-chloro-4-fluoro-5-[4-(fluoromethyl)-1-methyl-5-(trifluoromethyl)-1H-pyrazol-3-yl]benzoic acid, 1-methylethyl ester.

These compounds collectively provide out-standing control of resistant broadleaf weeds such as pigweed, cocklebur, velvetleaf and hemp sesbania in various crops such as corn, soybean and nuts and in forestry against trees and vines. Other of the compounds of this invention exhibit excellent herbicidal effect against weeds in other crops such as wheat and barley.

Some of the compounds of the present invention may have more than one possible stereoisomer and these stereoisomers may differ in herbicidal efficacy. The structures illustrated are intended to include all possible stereoisomers.

The above compounds may be suitably applied in a variety of application modes, e.g., pre-emergent and/or postemergent, surface applied, pre-plant incorporated, etc.

Another aspect of this invention relates to processes for preparing the compounds according to Formulae I and II and their precursors, intermediates and/or starting materials. Process I details the conversion of 4-halopyrazoles to 4-alkylpyrazoles and related 4-substituted pyrazoles via a pyrazole anion intermediate. The anionic intermediate such as the 4-lithiopyrazole obtained from treatment of a 4-bromopyrazole with an alkyllithium reagent is important for the success of this process step. Although anions of pyrazoles are known for the 3 and 5 positions of the pyrazole ring, anions of the 4 position of 5-haloalkylpyrazoles are novel (Heterocycles (1994), 37, 2087–2147). Pyrazoles having a hydrogen substituent in the four position do not provide 4-lithiopyrazoles on treatment with alkyllithium bases. The halogen in the four position was required for this transformation via a halogen-metal exchange. The anionic intermediate must be treated with a suitable electrophile prior to regiochemical scrambling of the pyrazole anion in order to obtain 4-substituted pyrazoles as the major product.

Process II describes a cyclocondensation route towards 4-alkylpyrazoles from a ketovinylether of Formula C and either hydrazine or an alkylhydrazine. Cyclocondensation of allyl substituted diketones with hydrazine to give 4-allyl-5-trifluoromethylpyrazoles is known (Synthesis, 1986, 340), however, routes towards 3-aryl-4-alkyl-5-trifluoromethylpyrazoles were previously unknown. The cyclocondensation described in Process II is a unique method utilizing ketovinylethers of Formula C to provide direct access to compounds of Formula I.

Process III describes transformations of the novel compounds of Formula I to various derivatives having desired carbon substitutions in the 5-position of the phenyl ring. Process IV describes the conversion of new compounds of Formula I (where $R_3$ is CHO) to 4-fluoromethylpyrazoles and 4-difluoromethylpyrazoles. These process aspects will be discussed in more detail below.

Other aspects of this invention relate to herbicidal compositions containing the compounds of Formulae I and II and to herbicidal methods of using those compositions to control undesirable weeds.

It is further within the purview of this invention that the substituted-arylpyrazole compounds of Formulae I and II be formulated in compositions containing other herbicidal compounds as co-herbicides, e.g., acetamides, esp., acetanilides, thiocarbamates, ureas, sulfonylureas, sulfonamides, imidazolinones, benzoic acid and its derivatives, diphenyl ethers, salts of glyphosate, etc.

Other additaments may be included in such herbicidal formulations as desired and appropriate, e.g, plant disease control agents, such as fungicides, insecticides, nematicides and other pesticides.

As used herein, the terms "alkyl", "alkenyl", alkynyl" when used either alone or in compound form, e.g., haloalkyl, haloalkenyl, alkoxy, alkoxyalkyl, etc., are intended to embrace linear or branched-chain members. Preferred alkyl members are the lower alkyls having from 1 to 4 carbon atoms and preferred alkenyl and alkynyl members are those having from 2 to 4 carbon atoms.

The term "haloalkyl" is intended to mean alkyl radicals substituted with one or more halogen (chloro, bromo, iodo or fluoro) atoms; preferred members of this class are those having from 1 to 4 carbon atoms, especially the halomethyl radicals, e.g., trifluoromethyl. In polyhaloalkyl members, the halogens can all be the same or mixed halogens.

Representative, non-limiting alkyl, alkenyl, alkynyl, cycloalkyl, cycloalkylalkyl, cycloalkenyl and cycloalkenylalkyl members include the following:

Methyl, ethyl, the isomeric propyls, butyls, pentyls, hexyls, heptyls, octyls, nonyls, decyls, etc.; vinyl, allyl, crotyl, methallyl, the isomeric butenyls, pentenyls, hexenyls, heptenyls, octenyls; ethynyl, the isomeric propynyls, butynyls, pentynyls, hexynyls, etc.; the alkoxy, polyalkoxy, alkoxyalkyl and polyalkoxyalkyl analogs of the foregoing alkyl groups, e.g., methoxy, ethoxy, propoxys, butoxys, pentoxys and hexoxys and corresponding polyalkoxys and alkoxyalkyls, e.g., methoxymethoxy, methoxyethoxy, ethoxymethoxy, ethoxy-ethoxy, methoxymethyl, methoxyethyl, ethoxymethyl, ethoxyethyl, propoxymethyl, isopropoxymethyl, butoxymethyl, isobutoxymethyl, tertbutoxymethyl, pentoxymethyl, hexoxymethyl, etc., cyclopropyl, cyclobutyl, cyclopentyl, cyclohexyl, cycloheptyl, cyclopropylmethyl, cyclobutylmethyl, cyclopentylmethyl, etc.; the isomeric cyclopentenes, cyclohexenes and cycloheptenes having mono- or di-unsaturation; representative aryl, aralkyl and alkaryl groups include phenyl, the isomeric tolyls and xylyls, benzyl, naphthyl, etc.

Representative mono-, di- and tri- haloalkyl members include: chloromethyl, chloroethyl, bromomethyl, bromoethyl, iodomethyl, iodoethyl, chloropropyl, bromopropyl, iodopropyl, 1,1,-dichloromethyl, 1,1-dibromomethyl, 1,1-dichloropropyl, 1,2-dibromopropyl, 2,3-dibromopropyl, 1-chloro-2-bromoethyl, 2-chloro-3-bromopropyl, trifluoromethyl, trichloromethyl, etc.

Representative heterocyclic members include: alkylthiodiazolyl; piperidyl; piperidylalkyl; dioxolanylalkyl, thiazolyl; alkylthiazolyl; benzothiazolyl; halobenzothiazolyl; furyl; alkyl-substituted furyl; furylalkyl; pyridyl; alkylpyridyl; alkyloxazolyl; tetrahydrofurylalkyl; 3-cyanothienyl; thienylalkyl; alkyl-substituted thienyl; 4,5-polyalkylenethienyl; piperidinyl; alkylpiperidinyl; pyridyl; di- or tetrahydropyridinyl; alkyltetrahydromorpholyl; alkylmorpholyl; azabicyclononyl; diazabicycloalkanyl, benzoalkylpyrrolidinyl; oxazolidinyl; perhydrooxazolidinyl; alkyloxazolidyl; furyloxazolidinyl, thienyloxazolidinyl, pyridyloxazolidinyl, pyrimidinyloxazolidinyl, benzooxazolidinyl, $C_{3-7}$ spirocycloalkyloxazolidinyl, alkylaminoalkenyl; alkylideneimino; pyrrolidinyl; piperidonyl; perhydroazepinyl; perhydroazocinyl; pyrazolyl; dihydropyrazolyl; piperazinyl; perhydro-1,4-diazepinyl; quinolinyl, isoquinolinyl; di-, tetra- and perhydroquinolyl- or -isoquinolyl; indolyl and di- and perhydroihdolyl and said heterocyclic members substituted with radicals such as defined in Formula I.

By "agriculturally-acceptable salts" of the compounds defined by the above formulae is meant a salt or salts which readily ionize in aqueous media to form a cation or anion of said compounds and the corresponding salt anion or cation, which salts have no deleterious effect on the herbicidal properties of a given herbicide and which permit formulation of various mixtures, e.g., herbicide-antidote compositions without undue problems of mixing, suspension, stability, applicator equipment use, packaging, etc.

By "herbicidally-effective" is meant the amount of herbicide required to effect a meaningful injury or destruction to a significant portion of affected undesirable plants or weeds. Although of no hard and fast rule, it is desirable from a commercial viewpoint that 80–85% or more of the weeds be destroyed, although commercially significant suppression of weed growth can occur at much lower levels, particularly with some very noxious, herbicide-resistant plants.

DETAILED DESCRIPTION OF THE INVENTION

The compounds according to this invention are suitably prepared by a variety of processes as will be described below. The phenylpyrazoles of Formula A required for preparation of compounds of Formula I by Process I were obtained as previously described in U.S. Pat. No. 5,281,571. Compounds of Formula B were either known in the art or obtained by the methods described in copending U.S. Ser. Nos. 08/277,724 and 08/277,725 both filed on Jul. 20, 1994.

Process I

This process describes the preparation of compounds of Formula I from compounds of Formula A wherein Z is chlorine, bromine or iodine.

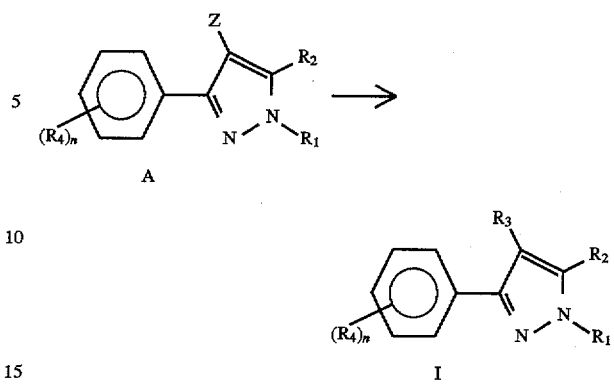

In this process description, compounds of Formula I are prepared by treatment of compounds of Formula A with a suitable base, sequential addition of bases or combination of bases followed by treatment with an alkylating agent or electrophile. Any inert solvent may be used in this reaction that does not markedly hinder the reaction from proceeding. Such solvent include, but are not limited to, ethers, cyclic ethers, polyethers, hydrocarbons and aromatic hydrocarbons. The base may be chosen from any number of alkyl lithium, aryllithium, Grignard or other reagents capable of replacing the halogen Z group of Formula A. In addition, base combinations can be used to improve overall conversion or yield. Acidic functionality in the substrate which would otherwise be incompatable with this transformation, such as compounds of Formula A wherein $R_4$ is a COOH group, can be protected by formation of a salt such as the lithium, sodium or magnesium carboxylate salts. This can be achieved by addition of excess base or initial formation of the carboxylate salt with bases such as, but not limited to, sodium hydride, lithium hydride, alkyllithium, aryllithium, Grignard reagents, etc. The amount of base or combination of bases can range from less than one molar equivalent to an excess. The intermediate anionic or dianionic species obtained after addition of base is treated with an alkylating agent or suitable electrophile such as methyl iodide, dimethylsulfoxide, dimethylformamide, etc. The amount of alkylating agent or suitable electrophile can range from less than one molar equivalent to an excess. Reaction temperature is in the range of −150° C. to 100° C., preferably −110° C. to 0° C. The reaction period may be chosen from the range of a few minutes to several weeks depending on the amounts of reagents, reaction temperature, etc. After completion, the reaction mixture is treated with water or aqueous acid and the product is isolated by a method such a crystallization or solvent extraction. If necessary, the product is purified by standard methods.

Process II

This process describes the preparation of compounds of Formula I by a multi-step sequence from alkyl aryl ketones of Formula B. The ketone B is converted to a vinyl ether C wherein R is an alkyl or aryl group followed by either direct conversion to a compound of Formula I or a stepwise formation of pyrazole D followed by alkylation to give a compound of Formula I.

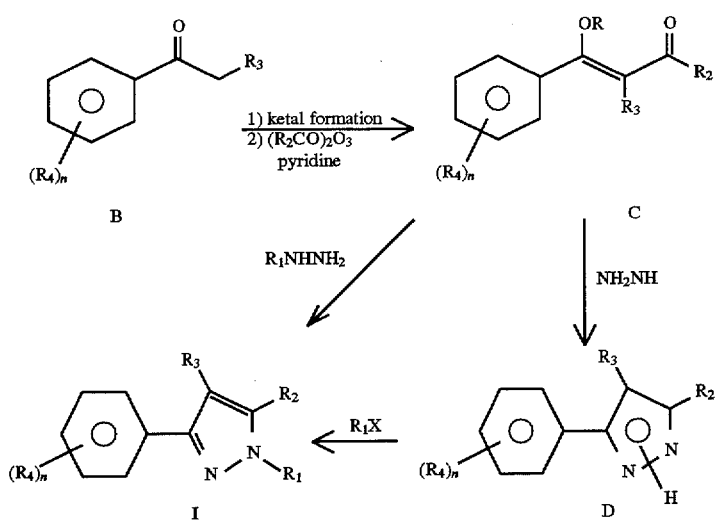

The alkyl aryl ketone B can be converted to a ketal by any of the methods known in the art. This is typically accomplished by addition of an alcohol or orthoformate to the ketone in the presence of an acid or acid catalyst. A preferred method is treatment of B with trialkyl orthoformate in the presence of a strong acid such as, but not limited to, mineral acid, sulfuric acid, gaseous HCl, etc. Removal of water from the reaction mixture will improve the reaction rate and yields of ketals. The ketal is treated with a haloalkyl anhydride in the presence of pyridine following the method of Hojo, et. al. (*Synthesis*, 1986, p. 1013). A vinyl ether C is obtained which can be treated with hydrazine or a (halo) alkylhydrazine in any suitable solvent to give pyrazole D or a compound of Formula I, respectively. The reaction temperature for this cyclocondensation step is in the range of −78° C. to 200° C., preferably 10°C. to 120° C. The reaction period may be chosen from the range of a few minutes to several weeks depending on the amounts of reagents, reaction temperature, etc. The product is isolated after completion of the reaction by filtration and/or concentration of the reaction mixture. If necessary, the product is purified by standard methods such as extraction, crystallization, column chromatography, etc.

In the case of addition of hydrazine to compounds of Formula C, the resultant pyrazole of Formula D may be treated with an alkylating agent to obtain compounds of Formula I. The alkylating agents suitable for this reaction include methyl iodide, allyl bromide, dimethylsulfate, etc. Preferred solvents are toluene, dimethylsulfoxide, acetone dimethylformamide, dioxane, etc. The reaction may be carried out with or without a base. In cases in which a base is employed, alkali metal carbonates or hydroxides such as sodium carbonate or sodium hydroxide may be used. Reaction temperature is in the range of −78° C. to 200° C., preferably 10° C. to 120° C. The reaction period may be chosen from the range of a few minutes to several weeks depending on the amounts of reagents, reaction temperature, etc. The product is isolated after completion of the reaction by filtration and/or concentration of the reaction mixture. If necessary, the product is purified by standard methods such as extraction, crystallization, column chromatrography, etc.

Process III

This process describes the conversion of compounds of Formula II wherein $R_7$ is a carboxylic acid, to various derivatives of Formula I compounds such as benzyl esters, amides, benzyl alcohols, benzyl halides or benzyl (thio) ethers ($R_7$ is an ester, amide, hydroxyalkyl, haloalkyl, alkoxyalkyl or thioalkyl radical). The compounds of Formula II, wherein $R_7$ is COOH, require starting materials obtained by either Process I or II.

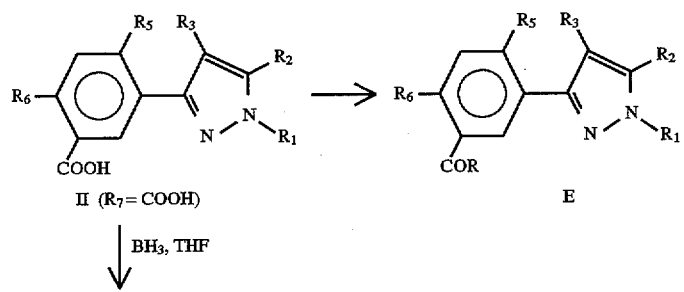

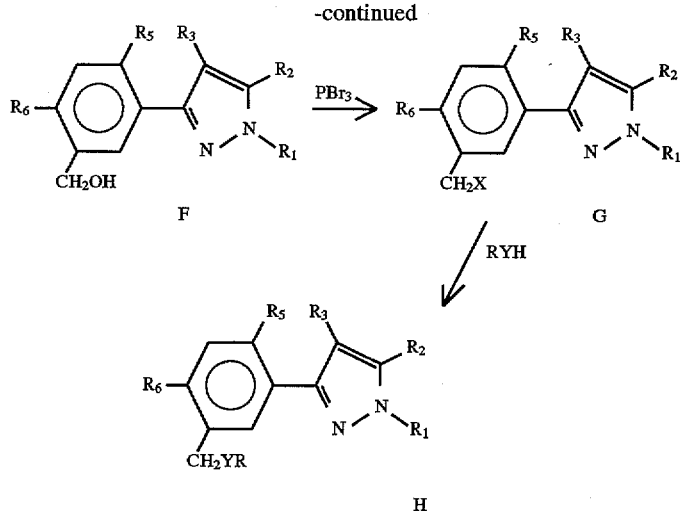

Compounds of Formula E, wherein R is $YR_{10}$ or $NR_{11}R_{12}$, are obtained from compounds of Formula I, wherein $R_7$ is COOH, by one of the standard methods for preparation of derivatives of carboxylic acids. This process step is an esterification or an amide-forming reaction. This may be accomplished directly from carboxylic acid or its alkali metal salt. The esterification can be carried out by using an excess of the alcohol corresponding to the objective ester in the presence of a mineral acid (e.g., sulfuric acid). The amide derivatives can be prepared by treating the carboxylic acid with the desired amine either neat or in a suitable solvent. The esterification or amide-forming reactions can also be carried out in the presence of an inert solvent and a dehydrating agent.

Alternatively, compounds of Formula II, wherein $R_7$ is COOH, can be converted to an acid halide or anhydride and treated with an alcohol or amine. Preparation of the acid halide is carried out in the presence of a halogenating agent such as, but not limited to, thionyl chloride, phosphorus pentachloride, oxalyl chloride, etc, with or without an inert solvent. Any inert solvent which does not interfere with the reaction may be employed. A catalytic amount of an amine base such as triethylamine, pyridine or dimethylformamide or the like may be added for the purpose of promoting this reaction. The reaction temperature is in the range of $-20°$ C. to the boiling point of the solvent used. The reaction period ranges from several minutes to 48 hours depending upon the amounts of reactants used and the reaction temperature. After completion of the reaction, the excess halogenating reagent and solvent(s) are removed from the reaction product by evaporation or distillation. The resultant acid halide may be subjected to an amine or alcohol directly and purified by the usual means.

The acid halide is treated with an alcohol or amine to give a compound or Formula E. Any inert solvent may be employed and a catalytic amount of an amine base such as triethylamine, pyridine or dimethylformamide or the like may be added for the purpose of promoting this reaction. The reaction temperature is in the range of $-20°$ C. to the boiling point of the solvent used. The reaction period ranges from several minutes to 48 hours depending upon the amounts of reactants used and the reaction temperature. The product is isolated after completion of the reaction by filtration and/or concentration of the reaction mixture. If necessary, the product is purified by standard methods such as extraction, crystallization, column chromatography, etc.

Compounds of Formula F can be prepared by reduction of the carboxylic acid group of compounds of Formula I using a reducing agent such as diborane, borane-tetrahydrofuran, borane complex, lithium aluminum hydride, aluminum hydride, etc. Conversion of the benzyl alcohol to a benzyl halide of Formula G can be carried out with any of a number of halogenated reagents such as hydrogen halides or inorganic acid halides, including phosphorus tribromide, thionyl chloride, phosphorus oxychloride, phosphorus pentachloride, hydrogen bromide, hydrogen iodide, etc. Compounds of Formula G can be converted to compounds of Formula H by displacement of the halogen radical X by a suitable nucleophile. Formation of products of Formula H can be carried out by treatment of compounds of Formula G with an alkoxide, thioalkoxide, amine, alkyl or aryl anion etc., or an alcohol, mercaptan, amine, etc. in the presence of a base in any suitable solvent. The preferred solvents are dimethylsulfoxide, acetone dimethylformamide, dioxane, etc. The base may be an organic base (such as a trialkylamine or another organic amine) or an inorganic base (an alkali carbonate such as potassium carbonate or sodium carbonate). Reaction temperature is in the range of $0°$ C. to $150°$ C., preferably $10°$ to $100°$ C. The reaction period may be chosen from the range of a few minutes to several weeks depending on the amounts of reagents, reaction temperature, etc. The product is isolated after completion of the reaction by filtration and/or concentration of the reaction mixture. If necessary, the product is purified by standard methods such as extraction, crystallization, column chromatography, etc.

Process IV

This section describes a process for the preparation of compounds of Formulae J, K and L from compounds of Formula I wherein the $R_3$ radical is a CHO group. The compounds of Formula I wherein $R_3$ is a CHO group are obtained by Process I.

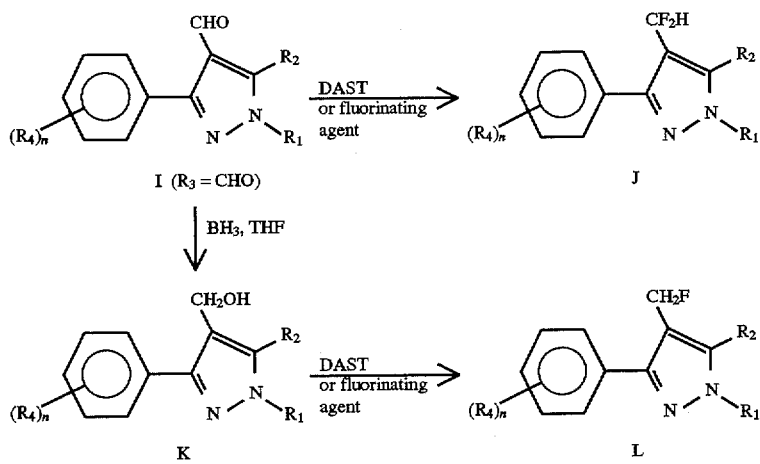

In this process, compounds of Formula J are prepared by fluorination of the aldehyde group of compounds of Formula I with a suitable fluorinating agent. Any solvent may be employed which does not interfer with the course of the reaction. Fluorinating reagents include, but are not limited to, diethylaminosulfur trifluoride (DAST), dialkylaminosulfur trifluorides, $SF_4$, HF, $SeF_4$, $PhSF_3$, $MoF_6$, etc. Compounds of Formula K can be prepared by reduction of the aldehyde group of compounds of Formula I ($R_3$ is CHO) using a reducing agent such as diborane, borane-tetrahydrofuran, borane complex, lithium aluminum hydride, aluminum hydride, etc. Compounds of Formula K are prepared by fluorination of compounds of Formula J with a suitable fluorinating agent. Fluorinating reagents include, but are not limited to, diethylaminosulfur trifluoride (DAST), dialkylaminosulfur trifluorides, $SF_4$, HF, $SeF_4$, $PhSF_3$, $MoF_6$, etc. Any of the products J, K or L are isolated after completion of the reaction by filtration and/or concentration of the reaction mixture. If necessary, the product is purified by standard methods such as extraction, crystallization, column chromatography, etc.

Further derivatives of compounds obtained by the above Processes I–IV can be prepared by any of the processes or methods outlined in U.S. Pat. No. 5,281,571 which is incorporated by reference.

The following Examples 1–15 describe specific working embodiments for the preparation of representative compounds according to this invention.

Examples 1 through 3 describe specific working embodiments of Process I.

EXAMPLE 1

Preparation of 3-(2,5-Difluorophenyl)-1,4-dimethyl-5-(trifluoromethyl)-1H-pyrazole A solution of 10 g of 4-bromo-3-(2,5-difluorophenyl)-1-methyl-5-(trifluoromethyl)-1H-pyrazole in 250 mL anhydrous THF was cooled to −78° C. and stirred with an overhead stirrer. The cold solution was treated with 12 mL of 2.5M n-butyllithium in hexanes never allowing the temperature to exceed −70° C. After stirring for 5 minutes, 1.9 mL of methyl iodide was added quickly. The cooling bath was removed and the solution allowed to warm to room temperature. The solution was diluted with diethyl ether and the combined organic extracts were washed twice with brine, dried over anhydrous magnesium sulfate and concd in vacuo. Chromatographic purification (silica, 5% ethyl acetate in hexanes) gave 5.8 g (72.4%) of 3-(2,5-difluorophenyl)-1,4-dimethyl-5-(trifluoromethyl)-1H-pyrazole as an oil; 1HNMR (CDCl3) δ 2.0 (quintet, 3H, J=2.1 Hz), 3.9 (d, 3H, J=1.2 Hz), 6.9–7.1 (m, 3H). Anal. Calcd for C13H9F5N2: C, 52.18; H, 3.28; N, 10.14. Found: C, 52.20; H, 3.30; N, 10.11.

EXAMPLE 2

Preparation of 2-Chloro-5-[1,4-dimethyl-5-(trifluoromethyl)-1H-pyrazol-3-yl]-4-fluorobenzoic acid A solution of 30 g of 5-[4-bromo-1-methyl-5-(trifluoromethyl)-1H-pyrazol-3-yl]-2-chloro-4-fluorobenzoic acid in 800 mL of anhydrous THF was stirred with a mechanical stirrer and treated with 3.36 g of 80% NaH. The stirred mixture was kept under a nitrogen atmosphere and heated to 60° C. for one hour. After formation of the sodium carboxylate salt, the mixture was cooled to −110° C. and 32.3 mL of 2.5M n-butyllithium in hexanes was added never allowing the temperature to exceed −100° C. The reaction was stirred at −110° C. for ten minutes, subsequently treated with 9.3 mL of methyl iodide and allowed to warm to room temperature. The mixture was quenched with 3N HCl and the volatiles removed. A precipitate formed which was collected and recrystallized from ethanol/water to give 24.5 g of a white solid: mp 155.0° C.; 1HNMR (CDCl3) δ 2.06 (m, 3H), 4.01 (s, 3H), 7.27 (d, 1H, J=9.6 Hz), 8.17 (d, 1H, J=7.6 Hz). Anal. Calcd for $C_{13}H_9O_2Cl_1N_2F_4$: C, 46.38; H, 2.69; N, 8.32. Found: C, 46.46; H, 2.65; N, 8.33.

EXAMPLE 3

Preparation of 2-Chloro-4-fluoro-5-[4-formyl-1-methyl-5-(trifluoromethyl)-1H-pyrazol-1-3-yl] benzoic acid To a mechanically stirred solution of 10 g of 5-[4-bromo-1-methyl-5-(trifluoromethyl)-1H-pyrazol-3-yl]-2-chloro-4-fluorobenzoic acid in 400 ml of anhydrous tetrahydrofuran under a nitrogen atmosphere was added 1.0 g of 95% sodium hydride. After the foaming subsided, the reaction was stirred and heated to 60° C. for one hour to ensure complete anion formation of the acid. The reaction was cooled to −110° C. with vigorous stirring and a 10.8 mL of 2.5M n-butyl lithium in hexanes was added maintaining the temperature below −100° C. As soon as the addition of n-butyl lithium was completed, 10 mL of dimethyl formamide was added and the solution was allowed to warm to −20° C. The reaction was then quenched with 3N HCl, and most of the volatiles were removed from the reaction mixture. The precipitate was filtered and recrystalized from carbon tetrachloride to give 3.0 g of 2-chloro-4-fluoro-5-[4-formyl-1-methyl-5-(trifluoromethyl)-1H-pyrazol-3-yl]benzoic acid: mp 163° C.; $^1$HNMR (CDCl$_3$) ppm: 9.82 (s, 1H), 7.89 (d, 1H, J=7.6), 7.07 (d, 1H, J=9.2), 3.39 (s, 3H). $^{19}$FNMR (CDCl$_3$) ppm: −57.78, −107.41.

Examples 4 through 7 describe specific working embodiments of Process II.

EXAMPLE 4

Preparation of 1-Chloro-4-(1,1-diethoxypropyl) benzene

A solution of 15.0 g of p-chloropropiophenone and 7.8 mL of dry EtOH was treated with 22.0 mL of triethyl orthoformate. Gaseous HCl was bubbled through the solution until saturation and the reaction mixture heated to reflux overnight. An additional 14.8 mL. Of triethyl orthoformate was added and the reaction mixture allowed to cool to room temperature. The cooled mixture was washed with 10% Na$_2$CO$_3$, extracted with diethyl ether and concd in vacuo to afford 19.0 g (88%) of a crude orange/yellow oil. The oil was distilled and a fraction collected (75°–96° C., 100 mtorr) which contained 13.4 g of 1-chloro-4-(1,1-diethoxypropyl) benzene: µ (23,D) 1.5612; $^1$HNMR (CDCl$_3$) δ 0.56 (t, 3H, 7.5 Hz), 1.19 (t, 6H, 7.0 Hz), 1.89 (q, 2H, 7.5 Hz), 3.36 (m, 4H), 7.28 (d, 2H, 8.5 Hz), 7.42 (d, 2H, 8.5 Hz). Anal. Calcd for C$_{13}$H$_{19}$O$_2$Cl: C, 64.32; H, 7.89. Found: C, 64.09; H, 7.81.

EXAMPLE 5

Preparation of 4-(4-Chlorophenyl)-4-ethoxy-1,1,1-trifluoro-3-methyl-3-buten-2-one.

A solution of 2.0 g of 1-chloro-4-(1,1-diethoxypropyl) benzene and 2.5 mL of CH$_2$Cl$_2$ was treated with 1.45 mL of pyridine. The solution was cooled to 0° C. and treated with 5.5 mL of (CF$_3$CO)$_2$O in 2.5 mL of CH$_2$Cl$_2$. After heating overnight at reflux, the reaction mixture was cooled, diluted with CH$_2$Cl$_2$ and 12 mL of ice cold water was added. The organic layer was seperated and washed with 20 mL of 1N HCl, followed by a washing with 20 mL of 10% Na$_2$CO$_3$ and two washing with 20 mL of water. The organic layer was dried over Na$_2$SO$_4$ and concd in vacuo to yield 1.69 g of a dark brown oil. Chromatographic purification (silica, 10% ethyl acetate in hexanes) yielded 1.0 g of a yellow oil. Bulb to bulb distillation gave 0.45 g of a very pure light yellow oil: µ(23,D) 1.5137; major geometric isomer: $^1$HNMR (CDCl$_3$) δ 1.22 (t, 3H, 7.0 Hz), 1.70 (s, 3H), 3.64 (q, 2H, 7.0 Hz), 7.30 (d, 2H, 8.3 Hz), 7.46 (d, 2H, 8.4 Hz). $^{19}$FNMR (CDCl$_3$) δ −74.68 (CF$_3$). Anal. Calcd for C$_{13}$H$_{12}$O$_2$F$_3$Cl: C, 53.35; H, 4.13. Found: C, 53.44; H, 4.10.

EXAMPLE 6

Preparation of 5-(4-Chlorophenyl)-4-methyl-3-(trifluoromethyl)-1H-pyrazole

A solution of 5.5 g of 4-(4-chlorophenyl)-4-ethoxy-1,1,1-trifluoro-3-methyl-3-buten-2-one in 20 mL of MeOH was slowly treated with 0.70 mL of NH$_2$NH$_2$ and allowed to stir for two hours. Water was added to the reaction mixture and a precipitate formed. The solid was collected by filtration and washed with hexanes to yield 3.87 g of 5-(4-chlorophenyl)-4-methyl-3-(trifluoromethyl)-1H-pyrazole as a white powdery product: mp 139.0° C.; $^1$HNMR (CDCl$_3$) δ 2.09 (s, 3H), 7.39 (m, 2H), 7.45 (m, 2H, 8.5 Hz), 11.75 (bs, 1H). $^{19}$FNMR (CDCl$_3$) δ −62.34° (3F). Anal. Calcd for C$_{11}$H$_8$N$_2$F$_3$Cl: C, 50.69; H, 3.09; N, 10.57. Found: C, 50.68; H, 3.05; N, 10.81.

EXAMPLE 7

Preparation of 3-(4-chlorophenyl)-1,4-dimethyl-5-(trifluoromethyl)pyrazole

To a solution of 3.7 g of 5-(4-chlorophenyl)-4-methyl-3-(trifluoromethyl)-1H-pyrazole in 40 mL of acetone was added 5.9 g of potassium carbonate and 1.8 mL of methyl iodide. The mixture was allowed stir overnight at room temperature, filtered and concd in vacuo to give a white solid. This mixture of two isomeric pyrazoles was purified by chromatography on silica (5% ethyl acetate in hexanes) to give 1.8 g (high R$_f$) of 3-(4-chlorophenyl)-1,4-dimethyl-5-(trifluoromethyl)pyrazole and 2.15 g (low R$_f$) of 5-(4-chlorophenyl)-1,4-dimethyl-3-(trifluoromethyl)pyrazole. The low R$_f$ material was distilled bulb to bulb (0.1 torr) to give a white, crystalline solid: mp 52°–54° C.; $^1$HNMR (CDCl$_3$) δ 2.06 (q, 3H, J=1.0 Hz), 3.77 (s, 3H), 7.26 (d, 2H, J=8.5 Hz), 7.50 (d, 2H, J=8.4 Hz); $^{19}$FNMR (CDCl$_3$) δ −61.6 (3F). Anal. Calcd for C$_{12}$H$_{10}$N$_2$F$_3$Cl$_1$: C, 52.47; H, 3.677N, 10.20. Found: C, 52.51; H, 3.70; N, 10.18.

The chromatographically less retained component (high R$_f$) was recrystallized from hexanes to give 3-(4-chlorophenyl)-1,4-dimethyl-5-(trifluoromethyl)pyrazole as a white, crystalline solid; mp 87°–88.5° C.; $^1$HNMR (CDCl$_3$) δ 2.25 (q, 3H, J=1.9 Hz), 3.99 (s, 3H), 7.39 (d, 2H, J=8.4 Hz), 7.50 (d, 2H, J=8.5 Hz); $^{19}$FNMR (CDCl$_3$) δ −58.4 (3F). Anal. Calcd for C$_{12}$H$_{10}$N$_2$F$_3$Cl$_1$: C, 52.47; H, 3.67; N, 10.20. Found: C, 52.48; H, 3.71; N, 10.16.

Examples 8 through 12 describe specific working embodiments of Process III.

EXAMPLE 8

Preparation of 2-Chloro-5-[1,4-dimethyl-5-(trifluoromethyl)-1H-pyrazol-3-yl]4-fluorobenzoic acid, 1-methylethyl ester To a solution of 18 g of 2-chloro-5-[1,4-dimethyl-5-(trifluoromethyl)-1H-pyrazol-3-yl]-4-fluorobenzoic acid. (Ex. 2) in 400 mL of CH$_2$Cl$_2$ was added 10 g of oxalyl chloride and a few drops of DMF. After 20 minutes at room temperature, the reaction was heated to reflux for 2 hr and subsequently concd in vacuo. The resultant solid was dissolved in excess 2-propanol and heated overnight at reflux. The reaction mixture was concd, dissolved in ether, washed with 10% aq. NaOH and saturated brine and concd to give a solid. Recrystallization from cold hexanes gave 14 g of 2-chloro-5-[1,4-dimethyl-5-(trifluoromethyl)-1H-pyrazol-3-yl]-4-fluorobenzoic acid, 1-methylethyl ester: mp 72° C.; $^1$HNMR (CDCl$_3$) δ 1.36 (d, 6H, 6.4 Hz), 2.09 (quintet, 3H, 2.0 Hz), 5.25 (heptet, 1H, 6.0 Hz), 7.27 (d, 1H, 9.2 Hz), 7.94 (d, 1H, 7.6 Hz). Anal. Calcd for C$_{16}$H$_{15}$O$_2$N$_2$F$_4$Cl: C, 50.74; H, 3.99; N, 7.40. Found: C, 50.85; H, 4.02; N, 7.41.

EXAMPLE 9

Preparation of 2-Chloro-5-[1,4-dimethyl-5-(trifluoromethyl)-1H-pyrazol-3-yl]-4-fluorobenzenemethanol A solution of 1.5 g of 2-chloro-5-[1,4-dimethyl-5-(trifluoromethyl)-1H-pyrazol-3-yl]-4-fluorobenzoic acid (Ex. 2) in 30 mL of anhydrous THF was treated with 10 mL of 1.0M borane-THF solution and heated to reflux for 24 hr. The mixture was allowed to cool and added to ice water. A precipitate formed which was collected by filtration, washed with cold water and dried to give 1.3 g of 2-chloro-5-[1,4-dimethyl-5-(trifluoromethyl)-1H-pyrazol-3-yl]-4-fluorobenzenemethanol as a white solid: mp 58° C.; $^1$HNMR (CDCl$_3$) δ 2.09 (q, 3H), 4.00 (s, 3H), 4.75 (s, 2H), 7.20 (d, 1H), 7.57 (d, 1H).

EXAMPLE 10

Preparation of 3-[5-(Bromomethyl)-4-chloro-2-fluorophenyl]-1,4-dimethyl-5-(trifluoromethyl)-1H-pyrazole To a solution of 7.0 g of 2-chloro-5-[1,4-dimethyl-5-(trifluoromethyl)-1H-pyrazol-3-yl]-4-fluorobenzenemethanol in 200 mL of diethyl ether was added 30 mL of phosphorus tribromide and the mixture allowed to stir overnight. The reaction mixture was poured into ice water, the ether removed by concd in vacuo and the resultant solid collected by filtration. The solid was washed with water and air dried to give a quantitative yield of 3-[5-(bromomethyl)-4-chloro-2-fluorophenyl]-1,4-dimethyl-5-(trifluoromethyl)-1H-pyrazole: $^1$HNMR (CDCl$_3$) δ 2.17 (t. 3H, 2.0 Hz), 4.07 (s, 3H), 4.64 (s, 2H), 7.30 (d, 1H, 9.5 Hz), 7.62 (d, 1H, 7.5 Hz); $^{19}$FNMR (CDCl$_3$) δ −58.5 (s, 3F), −111.6 (s, 1F).

EXAMPLE 11

Preparation of 3-[(4-Chloro-2-fluoro-5-(methoxymethyl)phenyl]-1,4-dimethyl-5-(trifluoromethyl)-1H-pyrazole A solution of 0.5 g of 3-[5-(bromomethyl)-4-chloro-2-fluorophenyl]-1,4-dimethyl-5-(trifluoromethyl)-1H-pyrazole in 100 mL of methanol was treated with 0.5 g of potassium carbonate and heated to reflux for five days. The mixture was diluted with methanol-water and the resultant precipitate collected by filtration. The solid was washed with water and air dried to afford 0.30 g of 3-[(4-chloro-2-fluoro-5-(methoxymethyl)phenyl]-1,4-dimethyl-5-(trifluoromethyl)-1H-pyrazole as a white powder: mp 59° C.; $^1$HNMR (CDCl$_3$) δ 2.09 (t, 3H, 2.0 Hz), 3.44 (s, 3H), 4.00 (s, 3H), 4.53 (s, 2H), 7.20 (d, 1H, 9.6 Hz), 7.55 (d, 1H, 8.0 Hz).

EXAMPLE 12

Preparation of 2-Chloro-4-fluoro-5-[4-formyl-1-methyl-5-(trifluoromethyl)-1H-pyrazol-3-yl]benzoic acid, 1-methylethyl ester To a slurry of 2.5 g of 2-chloro-4-fluoro-5-[4-formyl-1-methyl-5-(trifluoromethyl)-1H-pyrazol-3-yl]benzoic acid (Ex. 3) in 50 ml of methylene chloride was added 10 mL of oxalyl chloride followed by catalytic DMF. The solution was stirred for one hour and concd in vacuo. The resultant residue was diluted in 2-propanol and heated to 50° C. for one hour. The reaction was poured onto water and extracted into diethyl ether. The combined organic extracts were washed with brine and 2.5N sodium hydroxide solution, dried and concd to give a material which contained the desired product and a bi-product. Chromatographic purification (silica, 10% ethyl acetate in hexanes) afforded 1.0 g of 2-chloro-4-fluoro-5-[4-formyl-1-methyl-5-(trifluoromethyl)-1H-pyrazol-3-yl]benzoic acid, 1-methylethyl ester in a 36% yield: mp 90° C.; $^1$HNMR (CDCl$_3$) δ 10.04 (s, 1H), 7.9 (d, 1H, J=7.6), 7.25 (d, 1H, J=9.2), 5.23 (m, 1H), 4.11 (s, 3H), 1.35 (d, 6H, J=6.0).

Examples 13 through 15 describe specific working embodiments of Process IV.

EXAMPLE 13

Preparation of 2-Chloro-5-[4-(difluoromethyl)-1-methyl-5-(trifluoromethyl)-1H-pyrazol-3-yl]-4-fluorobenzoic acid, 1-methylethyl ester To a solution of 1.5 g of 2-chloro-4-fluoro-5-[4-formyl-1-methyl-5-(trifluoromethyl)-1H-pyrazol-3-yl]benzoic acid, 1-methylethyl ester in 50 mL methylene chloride was added 7 mL of diethyl aminosulfurtrifluoride and the solution stirred overnight at room temperature. The reaction was poured onto ice water and the organic layer was washed with brine, dried over anhydrous magnesium sulfate, filtered and concd in vacuo to give 1.0 g of 2-chloro-5-[4-(difluoromethyl)-1-methyl-5-(trifluoromethyl)-1H-pyrazol-3-yl]-4-fluorobenzoic acid, 1-methylethyl ester as a yellow solid: mp 57° C.; $^1$HNMR (CDCl$_3$) δ 8.06 (d, 1H, J=7.7), 7.36 (d, 1H, J=9.5), 6.75 (t, 1H, J=55.1), 5.32 (m, 1H, J=6.3), 4.16 (s, 3H), 1.42 (d, 6H, J=6.6). $^{19}$FNMR (CDCl$_3$) δ −58.56, −108.01, −109.53. Anal. Calcd for C$_{16}$H$_{13}$Cl$_1$F$_6$N$_2$O$_2$: C, 46.34; H, 3.16; N, 6.75. Found: C, 46.08; H, 3.25; N, 6.79.

EXAMPLE 14

Preparation of 2-Chloro-4-fluoro-5-[4-(hydroxymethyl)-1-methyl-5-(trifluoromethyl)-1H-pyrazol-3-yl]benzoic acid, 1-methylethyl ester To a solution of 0.5 g of 2-chloro-4-fluoro-5-[4-formyl-1-methyl-5-(trifluoromethyl)-1H-pyrazol-3-yl]benzoic acid, 1-methylethyl ester in 50 ml of anhydrous tetrahydrofuran was added 4 mL of 1M borane in THF solution. The reaction was stirred overnight and then poured onto water, extracted into diethyl ether, dried over anhydrous magnesium sulfate and concd in vacuo to give 0.5 g of 2-chloro-4-fluoro-5-[4-(hydroxymethyl)-1-methyl-5-(trifluoromethyl)-1H-pyrazol-3-yl]benzoic acid, 1-methylethyl ester as a clear oil: $^1$HNMR (CDCl$_3$) δ 8.10 (d, 1H J=7.7,), 7.36 (d, 1H, J=9.6), 5.29 (m, 1H), 4.62 (s, 2H), 4.10 (s, 3H), 1.42 (d, 6H, J=6.6); $^{19}$FNMR (CDCl$_3$) ppm: −58.82, −109.09.

EXAMPLE 15

Preparation of 2-Chloro-4-fluoro-5-[4-(fluoromethyl)-1-methyl-5-(trifluoromethyl)-1H-pyrazol-3-yl]benzoic acid, 1-methylethyl ester To a solution of 0.5 g 2-chloro-4-fluoro-5-[4-(hydroxymethyl)-1-methyl-5-(trifluoromethyl)-1H-pyrazol-3-yl]benzoic acid, 1-methylethyl ester in 50 ml methylene chloride was added 5 mL of diethyl aminosulfurtrifluoride and the solution stirred overnight at room temperature. The reaction mixture was poured onto ice water and the organic layer washed with brine, dried over anhydrous magnesium sulfate, filtered and the concd in vacuo to give 2-chloro-4-fluoro-5-[4-(fluoromethyl)-1-methyl-5-(trifluoromethyl)-1H-pyrazol-3-yl]benzoic acid, 1-methylethyl ester as a tan solid: mp 74° C.; $^1$HNMR (CDCl$_3$) δ 8.02 (d, 1H, J=8.0), 7.30 (d, 1H, J=9.6), 5.29 (d, 2H, J=48.0), 5.26 (m, 1H, J=6.0), 4.09 (s, 3H), 1.37 (d, 6H, J=6.4).

Table 1 shows examples of compounds prepared according to Processes I–IV. Examples 1 through 15 are described above. Example 16 was prepared by the four step procedure outlined in Process II (Examples 4–7) except that the starting material for the first step was 1-(4-chloro-2-fluoro-5-methylphenyl)-1-propanone. Examples 17–32 and 41–58 were prepared from Example 2 by methods described in Process III. Example 33 was prepared by Process I from 4-bromo-3-(4-chloro-2-fluoro-5-methylphenyl)-1-methyl-5-(trifluoromethyl)-1H-pyrazole. Example 34 was prepared in an analogous manner to Example 1 except that dimethylformamide was used in place of methyl iodide to quench the intermediate anion. Examples 35 through 40 were prepared from Example 1 by methods previously described in U.S. Pat. No. 5,281,571.

TABLE 1

3-SUBSTITUTED PHENYLPYRAZOLES

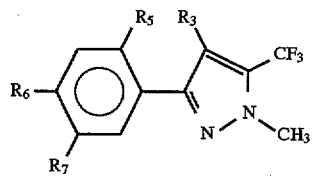

II ($R_1 = CH_3$; $R_2 = CF_3$)

| Cpd[a] No. | $R_3$ | $R_5$ | $R_6$ | $R_7$ | Physical Data[b] | Process |
|---|---|---|---|---|---|---|
| 1 | $CH_3$ | F | H | F | clear oil | I |
| 2 | $CH_3$ | F | Cl | COOH | 155° C. | I |
| 3 | CHO | F | Cl | COOH | 163° C. | I |
| 7 | $CH_3$ | H | Cl | H | 87–88.5° C. | II |
| 8 | $CH_3$ | F | Cl | $CO_2CH(CH_3)_2$ | 72° C. | III |
| 9 | $CH_3$ | F | Cl | $CH_2OH$ | 58° C. | III |
| 10 | $CH_3$ | F | Cl | $CH_2Br$ | c | III |
| 11 | $CH_3$ | F | Cl | $CH_2OCH_3$ | 59° C. | III |
| 12 | CHO | F | Cl | $COOCHMe_2$ | 90° C. | IV |
| 13 | $CHF_2$ | F | Cl | $COOCHMe_2$ | 57° C. | IV |
| 14 | $CH_2OH$ | F | Cl | $COOCHMe_2$ | oil | IV |
| 15 | $CH_2F$ | F | Cl | $COOCHMe_2$ | 74° C. | IV |
| 16 | $CH_3$ | OH | Cl | $CH_3$ | 109.5–110.5° C. | II |
| 17 | $CH_3$ | F | Cl | $CO_2CH_2CO_2Et$ | 55° C. | III |
| 18 | $CH_3$ | F | Cl | $CO_2CH_3$ | 62° C. | III |
| 19 | $CH_3$ | F | Cl | $CO_2$n-propyl | 60° C. | III |
| 20 | $CH_3$ | F | Cl | $CO_2CHMeCO_2Et$ | clear oil | III |
| 21 | $CH_3$ | F | Cl | $CONH_2$ | 135° C. | III |
| 22 | $CH_3$ | F | Cl | $CONH(CHMe_2)$ | 139° C. | III |
| 23 | $CH_3$ | F | Cl | $CO_2CH_2CO_2CHMe_2$ | 69° C. | III |
| 24 | $CH_3$ | F | Cl | $CO_2CH_2CH2CH_2CO_2Et$ | 50° C. | III |
| 25 | $CH_3$ | F | Cl | $CO_2$(3-tetrahydrofuranyl) | 76° C. | III |
| 26 | $CH_3$ | F | Cl | $CO_2Et$ | 60° C. | III |
| 27 | $CH_3$ | F | Cl | $CH_2SCH_3$ | white solid | II |
| 28 | $CH_3$ | F | Cl | $CH_2SO_2CH_3$ | white solid | III |
| 29 | $CH_3$ | F | Cl | $CH_2SCHMe_2$ | white solid | III |
| 30 | $CH_3$ | F | Cl | $CH_2SH$ | brown solid | III |
| 31 | $CH_3$ | F | Cl | $CH_2SCH_2CO_2CH_3$ | yellow oil | III |
| 32 | $CH_3$ | F | Cl | $CH_2SCH_2CHMe_2$ | yellow oil | III |
| 33 | $CH_3$ | F | Cl | $CH_3$ | 67–68° C. | I |
| 34 | CHO | F | H | F | clear oil | I |
| 35 | $CH_3$ | F | $NO_2$ | F | 65–67° C. | d |
| 36 | $CH_3$ | F | $NO_2$ | $OCH_3$ | 138° C. | d |
| 37 | $CH_3$ | F | Cl | $OCH_3$ | 89° C. | d |
| 38 | $CH_3$ | F | Cl | $OCH_2CO_2CHMe_2$ | 89° C. | d |
| 39 | $CH_3$ | F | Cl | $OCH_2C\equiv CH$ | 109° C. | d |
| 40 | $CH_3$ | F | Cl | OH | 115° C. | d |
| 41 | $CH_3$ | F | Cl | $CO_2CH_2Ph$ | e | III |
| 42 | $CH_3$ | F | Cl | $CO_2CH_2C\equiv CH$ | e | III |
| 43 | $CH_3$ | F | Cl | $CO_2CH_2COPh$ | e | III |
| 44 | $CH_3$ | F | Cl | $CO_2CH_2C(OMe)=CHCO_2Et$ | e | III |
| 45 | $CH_3$ | F | Cl | $CO_2CH_2CHMe_2$ | e | III |
| 46 | $CH_3$ | F | Cl | $CO_2CH_2CHEt_2$ | e | III |
| 47 | $CH_3$ | F | Cl | $CO_2CH_2$(2-morpholinyl) | e | III |
| 48 | $CH_3$ | F | Cl | $CO_2(CH_2)_4CH_3$ | e | III |

TABLE 1-continued

3-SUBSTITUTED PHENYLPYRAZOLES

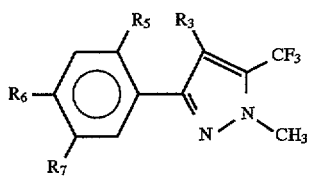

II ($R_1 = CH_3$; $R_2 = CF_3$)

| Cpd[a] No. | $R_3$ | $R_5$ | $R_6$ | $R_7$ | Physical Data[b] | Process |
|---|---|---|---|---|---|---|
| 49 | $CH_3$ | F | Cl | $CO_2(CH_2)_{11}CH_3$ | c | III |
| 50 | $CH_3$ | F | Cl | $CO_2CH_2SCN$ | c | III |
| 51 | $CH_3$ | F | Cl | $CO_2CH_2CH_2CHMe_2$ | c | III |
| 52 | $CH_3$ | F | Cl | $CO_2CHMeCH_2OMe$ | c | III |
| 53 | $CH_3$ | F | Cl | $CO_2(CH_2)_3COCH_3$ | c | III |
| 54 | $CH_3$ | F | Cl | $CO_2CH_2CH=CH_2$ | c | III |
| 55 | $CH_3$ | F | Cl | $CO_2(CH_2)_2CHMe_2$ | c | III |
| 56 | $CH_3$ | F | Cl | $CO_2(CH_2)_2OCH_3$ | c | III |
| 57 | $CH_3$ | F | Cl | $CO_2CH_2$(2-furanyl) | c | III |
| 58 | $CH_3$ | F | Cl | $CO_2CH(CH_3)Et$ | c | III |

[a]Compound numbers correspond to example numbers.
[b]Physical Data include melting point and physical appearance.
[c]No physical data were obtained.
[d]Prepared by methods in U.S. Pat. No. 5,281,571.

Pre-Emergence Herbicide Tests

As noted above, the compounds of this invention have been found to be surprisingly effective as herbicides.

The tests for pre-emergence herbicide activity were conducted according to the following methods:

Topsoil was placed in an aluminum pan and compacted to a depth of 1.3 to 1.6 cm from the top of the pan. On the top of the soil was placed a predetermined number of seeds of each of several monocotyledonous and dicotyledonous annual plant species and/or vegetative propagules of various perennial plant species. The pan was then level filled with a cover layer of topsoil to which was added a known amount of active ingredient either prior to or after application of the cover layer. The active ingredient was dissolved or suspended in an organic solvent, e.g., acetone, or water as carrier for application to the cover layer. The pans were moved to a greenhouse bench where they were thereafter watered from below as needed to give adequate moisture for germination and growth. In some cases, an initial overhead irrigation of ¼ inch of water was applied immediately after treatment.

Approximately 14 days after seeding and treating, the pans were observed and the results (% inhibition) were recorded.

The tables below summarize the results of the pre-emergence herbicidal activity tests of compounds of this invention tested with warm season plants (Tables 2a–2d) and cool season plants (Tables 3a and 3b). Table subdivisions a through d represent different spectra of plants tested. The herbicidal rating shown in these tables is the percent inhibition of each plant species. The plant species usually regarded as weeds are identified in the tables by single letter headings and crop species identified by two letter headings both headings being above the columns in accordance with the following legend:

Weed Species

A=Yellow Foxtail
B=Yellow Nutsedge
C=Barnyardgrass
D=Velvetleaf
E=Morning Glory
F=Cocklebur
G=Blackgrass
H=Common Chickweed
I=Bedstraw Catchweed
J=Broadleaf Signalgrass
K=Wild Proso Millet
L=Seedling Johnsongrass
M=Shattercane
N=Prickly Sida
O=Green Foxtail
P=Giant Foxtail
Q=Sicklepod
R=Black Nightshade
S=Hemp Sesbania
T=Wild Oats
U=Downy Brome
V=Birdseye Speedwell Crop Species AA=Rice
BB=Corn
CC=Soybean
DD=Wheat
EE=Rape Where noted in the tables below, the symbol "ND" indicates that the species was planted, but no data obtained for one reason or another.

TABLE 2a

PREEMERGENCE TESTS
% PLANT INHIBITION

| Cpd No. | Rate lb/A | A | B | C | D | E | F | AA | BB | CC |
|---|---|---|---|---|---|---|---|---|---|---|
| 1 | 4.5 | 35 | 45 | 50 | 65 | 35 | 0 | 0 | 10 | 0 |
|  | 0.893 | 0 | 0 | 0 | 0 | 0 | 0 | 25 | 0 | 0 |
| 34 | 4.5 | 20 | 20 | 0 | 75 | 0 | 0 | 0 | 0 | 0 |
|  | 0.893 | 0 | 0 | 0 | 15 | 0 | 0 | 0 | 0 | 0 |
|  | 0.1785 | 0 | 0 | 0 | 0 | 0 | 0 | 0 | 0 | 0 |
| 35 | 4.5 | 80 | 30 | 95 | 100 | 85 | 90 | 0 | 55 | 55 |
|  | 0.893 | 35 | 0 | 25 | 100 | 85 | 55 | 25 | 20 | 40 |
|  | 0.1785 | 0 | 0 | 0 | 98 | 80 | 60 | 0 | 5 | 0 |
|  | 0.893 | 35 | 40 | 0 | 98 | 80 | 35 | 0 | 5 | 25 |
|  | 0.1785 | 0 | 0 | 0 | 70 | 15 | 25 | 30 | 0 | 0 |
|  | 0.0357 | 0 | 0 | 0 | 0 | 0 | 0 | 0 | 0 | 0 |
| 36 | 0.893 | 100 | 0 | 100 | 100 | 90 | 85 | 65 | 90 | 10 |
|  | 0.1785 | 98 | 0 | 90 | 98 | 60 | 0 | 0 | 55 | 0 |
|  | 0.0357 | 15 | 0 | 20 | 20 | 10 | 20 | 0 | 10 | 0 |
|  | 0.0071 | 0 | 0 | 0 | 20 | 0 | 0 | 0 | 0 | 0 |
| 37 | 0.893 | 100 | 45 | 100 | 100 | 100 | 98 | 100 | 100 | 100 |
|  | 0.1785 | 100 | 50 | 100 | 100 | 90 | 80 | 85 | 85 | 50 |
|  | 0.0357 | 95 | 35 | 100 | 100 | 98 | 75 | 0 | 50 | 50 |
|  | 0.0071 | 55 | 0 | 80 | 98 | 80 | 100 | 25 | 25 | 20 |
| 38 | 0.893 | 65 | 85 | 70 | 100 | 100 | 90 | 40 | 40 | 70 |
|  | 0.1785 | 25 | 0 | 35 | 98 | 95 | 85 | 0 | 0 | 15 |
|  | 0.0357 | 0 | 20 | 15 | 80 | 75 | 65 | 0 | 0 | 5 |
|  | 0.0071 | 0 | 0 | 0 | 100 | 20 | ND | 0 | 0 | 0 |
| 39 | 0.893 | 100 | 65 | 100 | 100 | 100 | 100 | 100 | 100 | 100 |
|  | 0.1785 | 100 | 55 | 100 | 100 | 100 | 95 | 85 | 95 | 95 |
|  | 0.0357 | 100 | 25 | 100 | 100 | 85 | 80 | 70 | 80 | 100 |
|  | 0.0071 | 95 | 70 | 80 | 100 | 70 | 50 | 65 | 10 | 0 |
| 40 | 4.5 | 100 | 0 | 100 | 100 | 100 | 100 | 65 | 85 | 20 |
|  | 0.893 | 80 | 70 | 35 | 60 | 50 | 45 | 0 | 5 | 20 |
|  | 0.1785 | 0 | 0 | 0 | 0 | 0 | 0 | 0 | 0 | 0 |
|  | 0.0357 | 0 | 0 | 0 | 0 | 0 | 0 | 0 | 0 | 0 |

TABLE 2b

PREEMERGENCE TESTS
% PLANT INHIBITION

| Cpd No. | Rate lb/A | A | C | J | K | L | M | BB | CC |
|---|---|---|---|---|---|---|---|---|---|
| 37 | 0.5 | 100 | 100 | 100 | 100 | 100 | 100 | 98 | 80 |
|  | 0.25 | 100 | 100 | 100 | 100 | 100 | 100 | 95 | 35 |
|  | 0.125 | 100 | 100 | 100 | 100 | 100 | 100 | 85 | 10 |
|  | 0.0625 | 100 | 99 | 99 | 100 | 100 | 99 | 55 | 10 |
|  | 0.0313 | 99 | 70 | 85 | 95 | 99 | 90 | 45 | 0 |
|  | 0.0156 | 80 | 35 | 65 | 70 | 90 | 55 | 15 | 0 |
|  | 0.0078 | 85 | 70 | 75 | 90 | 75 | 60 | 20 | ND |
| 39 | 0.5 | 100 | 100 | 100 | 100 | 100 | 100 | 100 | 98 |
|  | 0.25 | 100 | 100 | 100 | 100 | 100 | 100 | 100 | 95 |
|  | 0.125 | 100 | 100 | 100 | 100 | 100 | 100 | 99 | 85 |
|  | 0.0625 | 100 | 100 | 100 | 100 | 100 | 100 | 90 | 40 |
|  | 0.0313 | 100 | 100 | 100 | 100 | 100 | 100 | 80 | 35 |
|  | 0.0156 | 100 | 99 | 99 | 100 | 95 | 99 | 35 | 25 |
|  | 0.0078 | 95 | 60 | 90 | 99 | 75 | 65 | 10 | 0 |

TABLE 2c

PREEMERGENCE TESTS
% PLANT INHIBITION

| Cpd No. | Rate lb/A | A | C | D | E | F | L | N | BB | CC |
|---|---|---|---|---|---|---|---|---|---|---|
| 38 | 0.5000 | 65 | 60 | 100 | 95 | 90 | 60 | 99 | 20 | 0 |
|  | 0.2500 | 40 | 20 | 100 | 100 | 70 | 30 | 95 | 5 | 0 |
|  | 0.1250 | 10 | 10 | 85 | 98 | 70 | 20 | 70 | 0 | 0 |
|  | 0.0625 | 0 | 0 | 90 | 90 | 30 | 0 | 70 | 0 | 0 |
|  | 0.0313 | 0 | 0 | 60 | 75 | 0 | 0 | 60 | 0 | 0 |
|  | 0.0156 | 0 | 0 | 65 | 55 | 0 | 0 | 50 | 0 | 0 |
|  | 0.0078 | 0 | 0 | 50 | 30 | 0 | 0 | 10 | 0 | 0 |

TABLE 2d

PREEMERGENCE TESTS
% PLANT INHIBITION

| Cpd No. | Rate lb/A | C | D | E | F | L | P | BB | CC |
|---|---|---|---|---|---|---|---|---|---|
| 2 | 0.25 | 0 | 50 | 35 | 35 | 20 | 0 | 0 | 5 |
|  | 0.0625 | 0 | 45 | 25 | 0 | 10 | 10 | 0 | 0 |
|  | 0.0156 | 0 | 10 | 0 | 0 | 0 | 0 | 0 | 0 |
|  | 1 | 15 | 70 | 60 | 15 | 25 | 0 | 0 | 45 |
|  | 0.5 | 0 | 35 | 60 | 0 | 0 | 0 | 0 | 0 |
|  | 0.25 | 0 | 20 | 30 | 0 | 0 | 0 | 0 | 0 |
|  | 0.125 | 0 | 0 | 0 | 0 | 0 | 0 | 0 | 0 |
|  | 0.063 | 0 | 0 | 0 | 0 | 0 | 0 | 0 | 0 |
|  | 0.031 | 0 | 0 | 0 | 0 | 0 | 0 | 0 | 0 |
| 3 | 0.25 | 15 | 25 | 60 | 5 | 25 | 5 | 0 | 20 |
|  | 0.0625 | 0 | 0 | 0 | 0 | 0 | 0 | 0 | 5 |
|  | 0.0156 | 0 | 0 | 0 | 0 | 0 | 0 | 0 | 0 |
|  | 0.0039 | 0 | 0 | 0 | 0 | 0 | 0 | 0 | 0 |
| 7 | 1 | 0 | 65 | 5 | 10 | 75 | 55 | 0 | 5 |
|  | 0.25 | 0 | 0 | 0 | 0 | 25 | 15 | 0 | 0 |

TABLE 2d-continued

PREEMERGENCE TESTS
% PLANT INHIBITION

| Cpd No. | Rate lb/A | C | D | E | F | L | P | BB | CC |
|---|---|---|---|---|---|---|---|---|---|
|  | 0.0625 | 0 | 0 | 0 | 0 | 0 | 0 | 0 | 0 |
| 8 | 0.25 | 100 | 98 | 45 | 80 | 100 | 100 | 85 | 30 |
|  | 0.0625 | 95 | 55 | 0 | 40 | 99 | 100 | 20 | 8 |
|  | 0.0156 | 30 | 5 | 0 | 20 | 70 | 90 | 5 | 0 |
|  | 0.5 | 100 | ND | 95 | 85 | 100 | 100 | 98 | 70 |
|  | 0.25 | 100 | ND | 80 | 75 | 100 | 100 | 90 | 50 |
|  | 0.125 | 100 | ND | 65 | 65 | 100 | 100 | 90 | 30 |
|  | 0.063 | 100 | ND | 30 | 50 | 99 | 99 | 25 | 20 |
|  | 0.031 | 60 | ND | 45 | 40 | 90 | 100 | 10 | 5 |
|  | 0.016 | 45 | ND | 20 | 25 | 90 | 95 | 0 | 0 |
|  | 0.25 | 100 | 100 | 100 | 99 | 100 | 100 | 70 | 80 |
|  | 0.125 | 99 | 100 | 99 | 93 | 100 | 100 | 25 | 60 |
|  | 0.063 | 88 | 93 | 60 | 63 | 93 | 100 | 23 | 30 |
|  | 0.031 | 43 | 80 | 90 | 53 | 93 | 100 | 15 | 18 |
|  | 0.016 | 20 | 60 | 45 | 10 | 58 | 93 | 3 | 15 |
|  | 0.008 | 5 | 30 | 38 | 0 | 15 | 45 | 5 | 0 |
|  | 0.25 | 100 | 100 | 100 | 75 | 100 | 100 | 100 | 45 |
|  | 0.0625 | 100 | 95 | 85 | 40 | 100 | 100 | 70 | 10 |
|  | 0.0156 | 55 | 85 | 50 | 20 | 90 | 98 | 15 | 0 |
|  | 0.0039 | 0 | 65 | 0 | 0 | 65 | 90 | 5 | 0 |
|  | 0.5 | 100 | 100 | 98 | 97 | 100 | 100 | 95 | 65 |
|  | 0.25 | 100 | 100 | 98 | 85 | 100 | 100 | 85 | 40 |
|  | 0.125 | 100 | 93 | 93 | 85 | 100 | 100 | 70 | 23 |
|  | 0.0625 | 99 | 70 | 55 | 60 | 100 | 100 | 35 | 8 |
|  | 0.0313 | 90 | 45 | 40 | 40 | 99 | 100 | 25 | 3 |
|  | 0.0156 | 75 | 45 | 45 | 25 | 98 | 97 | 10 | 5 |
|  | 0.0078 | 65 | 0 | 20 | 15 | 85 | 95 | 10 | 5 |
|  | 0.0039 | 40 | 0 | 0 | 0 | 75 | 80 | 5 | 0 |
| 9 | 0.25 | 95 | 98 | 5 | 10 | 85 | 65 | 7 | 0 |
|  | 0.0625 | 75 | 85 | 10 | 0 | 65 | 25 | 0 | 0 |
|  | 0.0156 | 0 | 50 | 0 | 0 | 15 | 0 | 0 | 0 |
| 10 | 0.25 | 20 | 99 | 40 | 50 | 35 | 35 | 5 | 0 |
|  | 0.0625 | 0 | 65 | 40 | 0 | 0 | 25 | 0 | 5 |
|  | 0.0156 | 0 | 0 | 0 | 0 | 0 | 0 | 0 | 0 |
|  | 0.0039 | 0 | 0 | 0 | 0 | 0 | 0 | 0 | 0 |
| 11 | 0.25 | 98 | 99 | 45 | 40 | 98 | 98 | 25 | 7 |
|  | 0.0625 | 80 | 85 | 30 | 25 | 85 | 80 | 5 | 0 |
|  | 0.0156 | 0 | 50 | 15 | 35 | 20 | 5 | 0 | 0 |
|  | 0.0039 | 0 | 10 | 0 | 0 | 0 | 0 | 0 | 0 |
| 12 | 0.25 | 95 | 95 | 45 | 45 | 98 | 98 | 5 | 35 |
|  | 0.0625 | 30 | 75 | 40 | 30 | 75 | 75 | 0 | 5 |
|  | 0.0156 | 0 | 0 | 0 | 0 | 50 | 65 | 0 | 0 |
|  | 0.0039 | 0 | 0 | 0 | 0 | 10 | 10 | 0 | 0 |
|  | 0.5 | 95 | 97 | 95 | 80 | 98 | 99 | 15 | 25 |
|  | 0.25 | 80 | 90 | 85 | 65 | 97 | 98 | 3 | 15 |
|  | 0.125 | 40 | 85 | 75 | 30 | 80 | 90 | 3 | 0 |
|  | 0.0625 | 35 | 50 | 25 | 35 | 85 | 85 | 0 | 0 |
|  | 0.0313 | 10 | 10 | 0 | 0 | 45 | 85 | 0 | 0 |
|  | 0.0156 | 5 | 0 | 0 | 0 | 30 | 75 | 0 | 0 |
|  | 0.0078 | 0 | 0 | 0 | 0 | 10 | 20 | 0 | 0 |
|  | 0.0039 | 0 | 0 | 0 | 0 | 10 | 20 | 0 | 0 |
| 13 | 0.25 | 100 | 100 | 80 | 70 | 100 | 100 | 80 | 30 |
|  | 0.0625 | 95 | 98 | 60 | 45 | 98 | 100 | 40 | 8 |
|  | 0.0156 | 30 | 80 | 35 | 0 | 90 | 90 | 10 | 8 |
|  | 0.0039 | 5 | 35 | 25 | 0 | 55 | 50 | 5 | 3 |
|  | 0.5 | 100 | 100 | 97 | 90 | 100 | 100 | 85 | 55 |
|  | 0.25 | 99 | 98 | 93 | 75 | 100 | 100 | 65 | 30 |
|  | 0.125 | 98 | 95 | 80 | 70 | 100 | 100 | 40 | 15 |
|  | 0.0625 | 90 | 80 | 75 | 65 | 99 | 99 | 35 | 5 |
|  | 0.0313 | 55 | 55 | 20 | 30 | 98 | 95 | 5 | 3 |
|  | 0.0156 | 30 | 35 | 0 | 10 | 85 | 95 | 3 | 5 |
|  | 0.0078 | 15 | 10 | 0 | 5 | 60 | 85 | 3 | 0 |
|  | 0.0039 | 0 | 0 | 0 | 0 | 25 | 25 | 0 | 0 |
| 14 | 0.25 | 90 | 60 | 40 | 15 | 97 | 98 | 15 | 8 |
|  | 0.0625 | 10 | 0 | 5 | 0 | 80 | 85 | 5 | 0 |
|  | 0.0156 | 0 | 0 | 0 | 0 | 50 | 50 | 0 | 0 |
|  | 0.0039 | 0 | 0 | 0 | 0 | 5 | 25 | 0 | 0 |
| 15 | 0.25 | 100 | 97 | 93 | 90 | 100 | 100 | 93 | 20 |
|  | 0.0625 | 98 | 65 | 65 | 40 | 100 | 100 | 30 | 15 |
|  | 0.0156 | 45 | 5 | 10 | 5 | 97 | 90 | 20 | 10 |
|  | 0.0039 | 0 | 10 | 20 | 5 | 35 | 55 | 5 | 0 |
| 16 | 0.25 | 0 | 0 | 0 | 0 | 0 | 0 | 0 | 0 |
|  | 0.0625 | 0 | 0 | 0 | 0 | 0 | 0 | 0 | 0 |
|  | 0.0156 | 0 | 0 | 0 | 0 | 0 | 0 | 0 | 0 |
| 17 | 0.25 | 0 | 50 | 50 | 10 | 5 | 40 | 0 | 5 |
|  | 0.0625 | 0 | 55 | 0 | 0 | 0 | 15 | 0 | 0 |
|  | 0.0156 | 0 | 25 | 0 | 0 | 0 | 0 | 0 | 0 |
| 18 | 0.25 | 95 | 98 | 45 | 20 | 90 | 95 | 15 | 15 |
|  | 0.0625 | 5 | 60 | 5 | 0 | 45 | 75 | 3 | 0 |
|  | 0.0156 | 0 | 20 | 0 | 0 | 0 | 15 | 0 | 0 |
|  | 1 | 100 | 100 | 95 | 70 | 99 | 100 | 80 | 80 |
|  | 0.5 | 100 | 100 | 80 | 80 | 100 | 100 | 30 | 20 |
|  | 0.25 | 99 | 98 | 55 | 25 | 95 | 100 | 25 | 0 |
|  | 0.125 | 90 | 95 | 50 | 15 | 65 | 95 | 50 | 0 |
|  | 0.063 | 55 | 90 | 55 | 20 | 70 | 80 | 0 | 0 |
|  | 0.031 | 15 | 50 | 10 | 0 | 30 | 45 | 0 | 0 |
|  | 0.25 | 93 | 100 | 100 | 53 | 85 | 99 | 65 | 40 |
|  | 0.125 | 60 | 98 | 75 | 25 | 45 | 65 | 8 | 10 |
|  | 0.063 | 10 | 93 | 55 | 20 | 10 | 30 | 5 | 10 |
|  | 0.031 | 0 | 43 | 55 | 0 | 0 | 20 | 0 | 0 |
|  | 0.016 | 0 | 50 | 25 | 10 | 0 | 0 | 3 | 0 |
|  | 0.008 | 5 | 30 | 25 | 0 | 30 | 3 | 3 | 3 |
| 19 | 0.25 | 98 | 90 | 35 | 60 | 95 | 99 | 25 | 10 |
|  | 0.0625 | 70 | 55 | 10 | 25 | 85 | 98 | 5 | 3 |
|  | 0.0156 | 15 | 15 | 0 | 15 | 20 | 55 | 0 | 0 |
|  | 0.25 | 95 | 98 | 93 | 70 | 85 | 100 | 28 | 28 |
|  | 0.125 | 65 | 100 | 95 | 75 | 85 | 99 | 13 | 13 |
|  | 0.063 | 20 | 78 | 70 | 30 | 48 | 85 | 3 | 10 |
|  | 0.031 | 0 | 45 | 30 | 0 | 20 | 73 | 3 | 10 |
|  | 0.016 | 10 | 0 | 0 | 0 | 30 | 60 | 0 | 0 |
|  | 0.008 | 0 | 0 | 0 | 0 | 5 | 0 | 0 | 0 |
| 20 | 0.25 | 95 | 95 | 85 | 55 | 85 | 98 | 15 | 5 |
|  | 0.0625 | 70 | 80 | 15 | 35 | 65 | 85 | 0 | 3 |
|  | 0.0156 | 0 | 20 | 0 | 0 | 5 | 30 | 0 | 0 |
|  | 0.5 | 85 | ND | 85 | 90 | 70 | 95 | 15 | 15 |
|  | 0.25 | 35 | ND | 70 | 55 | 25 | 80 | 10 | 5 |
|  | 0.125 | 10 | ND | 70 | 45 | 20 | 65 | 0 | 10 |
|  | 0.063 | 10 | ND | 50 | 0 | 20 | 65 | 0 | 5 |
|  | 0.031 | 0 | ND | 35 | 0 | 0 | 40 | 0 | 5 |
|  | 0.016 | 0 | ND | 0 | 0 | 0 | 40 | 0 | 0 |
| 21 | 0.25 | 90 | 25 | 20 | 20 | 85 | 45 | 10 | 15 |
|  | 0.0625 | 35 | 10 | 15 | 0 | 85 | 40 | 0 | 0 |
|  | 0.0156 | 0 | 0 | 0 | 0 | 5 | 10 | 0 | 0 |
| 22 | 0.25 | 95 | 40 | 5 | 25 | 97 | 98 | 5 | 25 |
|  | 0.0625 | 25 | 10 | 0 | 0 | 70 | 55 | 0 | 3 |
|  | 0.0156 | 0 | 0 | 0 | 0 | 0 | 0 | 0 | 0 |
| 23 | 0.25 | 40 | 65 | 25 | 10 | 30 | 65 | 0 | 5 |
|  | 0.0625 | 0 | 5 | 0 | 5 | 0 | 0 | 0 | 0 |
|  | 0.0156 | 0 | 0 | 0 | 0 | 0 | 0 | 0 | 0 |
| 24 | 0.25 | 20 | 60 | 0 | 40 | 10 | 35 | 0 | 0 |
|  | 0.0625 | 0 | 10 | 0 | 0 | 0 | 0 | 0 | 0 |
|  | 0.0156 | 0 | 0 | 0 | 0 | 0 | 0 | 0 | 0 |
| 25 | 0.25 | 95 | 80 | 55 | 35 | 99 | 100 | 45 | 5 |
|  | 0.0625 | 90 | 80 | 30 | 25 | 90 | 98 | 10 | 0 |
|  | 0.0156 | 25 | 25 | 0 | 10 | 35 | 85 | 5 | 0 |
|  | 0.0039 | 0 | 0 | 0 | 0 | 20 | 10 | 0 | 0 |
| 26 | 0.25 | 100 | 100 | 90 | 85 | 100 | 99 | 97 | 25 |
|  | 0.0625 | 98 | 97 | 65 | 35 | 98 | 97 | 65 | 0 |
|  | 0.0156 | 75 | 75 | 20 | 25 | 70 | 75 | 10 | 0 |
|  | 0.0039 | 10 | 40 | 10 | 10 | 35 | 25 | 3 | 0 |
|  | 0.5 | 100 | 100 | 99 | 99 | 100 | 100 | 98 | 60 |
|  | 0.25 | 100 | 100 | 97 | 93 | 100 | 100 | 95 | 75 |
|  | 0.125 | 100 | 100 | 80 | 88 | 100 | 100 | 85 | 53 |
|  | 0.063 | 100 | 97 | 60 | 65 | 100 | 100 | 50 | 18 |
|  | 0.031 | 95 | 97 | 43 | 53 | 90 | 87 | 10 | 5 |
|  | 0.016 | 85 | 93 | 30 | 40 | 85 | 90 | 8 | 5 |
|  | 0.25 | 100 | 100 | 98 | 92 | 100 | 99 | 33 | 72 |
|  | 0.125 | 100 | 100 | 100 | 90 | 100 | 100 | 70 | 73 |
|  | 0.063 | 98 | 100 | 90 | 68 | 97 | 100 | 25 | 25 |
|  | 0.031 | 70 | 83 | 73 | 30 | 75 | 65 | 18 | 18 |
|  | 0.016 | 35 | 83 | 58 | 25 | 43 | 50 | 8 | 3 |
|  | 0.008 | 0 | 15 | 13 | 10 | 0 | 15 | 0 | 0 |
| 27 | 0.25 | 60 | 90 | 75 | 20 | 90 | 50 | 5 | 3 |
|  | 0.0625 | 10 | 70 | 65 | 0 | 20 | 0 | 3 | 0 |
|  | 0.0156 | 0 | 30 | 0 | 0 | 0 | 0 | 0 | 0 |
|  | 0.0039 | 0 | 0 | 0 | 0 | 0 | 0 | 0 | 0 |

TABLE 2d-continued

PREEMERGENCE TESTS
% PLANT INHIBITION

| Cpd No. | Rate lb/A | C | D | E | F | L | P | BB | CC |
|---|---|---|---|---|---|---|---|---|---|
| 28 | 0.25 | 15 | 45 | 0 | 10 | 50 | 30 | 3 | 0 |
|  | 0.0625 | 0 | 0 | 0 | 0 | 20 | 20 | 0 | 0 |
|  | 0.0156 | 0 | 20 | 0 | 0 | 0 | 0 | 0 | 0 |
|  | 0.0039 | 0 | 25 | 0 | 0 | 0 | 0 | 0 | 0 |
| 29 | 0.25 | 80 | 70 | 65 | 15 | 100 | 95 | 30 | 20 |
|  | 0.0625 | 30 | 30 | 20 | 0 | 90 | 90 | 0 | 20 |
|  | 0.0156 | 0 | 10 | 0 | 0 | 10 | 10 | 0 | 0 |
|  | 0.0039 | 0 | 0 | 0 | 0 | 0 | 0 | 0 | 0 |
| 30 | 0.25 | 70 | 90 | 20 | 25 | 95 | 25 | 15 | 20 |
|  | 0.0625 | 5 | 70 | 30 | 10 | 90 | 25 | 3 | 5 |
|  | 0.0156 | 10 | 10 | 0 | 0 | 30 | 10 | 0 | 5 |
|  | 0.0039 | 0 | 0 | 0 | 0 | 15 | 0 | 0 | 0 |
| 31 | 0.25 | 5 | 80 | 45 | 15 | 40 | 10 | 10 | 3 |
|  | 0.0625 | 0 | 20 | 15 | 0 | 45 | 20 | 15 | 0 |
|  | 0.0156 | 0 | 5 | 0 | 0 | 0 | 0 | 0 | 0 |
|  | 0.0039 | 0 | 0 | 0 | 0 | 0 | 0 | 0 | 0 |
| 32 | 0.25 | 5 | 25 | 10 | 25 | 85 | 65 | 5 | 8 |
|  | 0.0625 | 0 | 0 | 5 | 0 | 30 | 10 | 3 | 0 |
|  | 0.0156 | 0 | 20 | 35 | 0 | 25 | 0 | 10 | 5 |
|  | 0.0039 | 0 | 0 | 0 | 0 | 25 | 0 | 0 | 0 |
| 33 | 0.25 | 65 | 85 | 25 | 35 | 90 | 65 | 10 | 5 |
|  | 0.0625 | 15 | 25 | 0 | 35 | 35 | 20 | 0 | 0 |
|  | 0.0156 | 0 | 0 | 0 | 0 | 0 | 0 | 0 | 0 |
|  | 0.25 | 0 | 55 | 0 | 10 | 0 | 0 | 0 | 0 |
|  | 0.125 | 0 | 0 | 0 | 0 | 0 | 0 | 0 | 0 |
|  | 0.063 | 0 | 0 | 0 | 0 | 0 | 0 | 0 | 0 |
|  | 0.031 | 0 | 0 | 0 | 0 | 0 | 0 | 0 | 0 |
|  | 0.016 | 0 | 0 | 0 | 0 | 0 | 0 | 0 | 0 |
|  | 0.008 | 0 | 0 | 0 | 0 | 0 | 0 | 0 | 0 |
|  | 1 | 99 | 100 | 98 | 50 | 99 | 95 | 45 | 20 |
|  | 0.5 | 95 | 100 | 98 | 65 | 98 | 95 | 20 | 10 |
|  | 0.25 | 70 | 100 | 80 | 50 | 95 | 95 | 10 | 5 |
|  | 0.125 | 35 | 95 | 70 | 30 | 70 | 95 | 5 | 5 |
|  | 0.063 | 45 | 100 | ND | 40 | 60 | 85 | 5 | 5 |
|  | 0.031 | 40 | 100 | ND | 60 | 55 | 90 | 10 | 5 |
|  | 0.016 | ND | 100 | ND | ND | ND | ND | 15 | 0 |
| 37 | 0.5 | 100 | 100 | 100 | 95 | 100 | 100 | 100 | 70 |
|  | 0.25 | 100 | 100 | 98 | 60 | 100 | 100 | 98 | 40 |
|  | 0.125 | 100 | 100 | 80 | 55 | 99 | 100 | 90 | 5 |
|  | 0.0625 | 99 | 85 | 75 | 30 | 98 | 100 | 80 | 0 |
|  | 0.0313 | 70 | 90 | 0 | 0 | 99 | 99 | 30 | 0 |
|  | 0.0156 | 15 | 60 | ND | 0 | 70 | 98 | 15 | 0 |
|  | 0.0078 | 0 | 0 | 0 | 0 | 15 | 80 | 0 | 0 |
| 38 | 0.5 | 10 | 80 | 85 | 75 | 35 | 50 | 5 | 0 |
|  | 0.25 | 0 | 80 | 95 | 85 | 25 | 20 | 0 | 0 |
|  | 0.125 | 0 | 50 | 80 | 25 | 0 | 0 | 0 | 0 |
|  | 0.0625 | 0 | 0 | 75 | 0 | 0 | 0 | 0 | 0 |
|  | 0.0313 | 0 | 0 | 0 | 0 | 0 | 0 | 0 | 0 |
|  | 0.0156 | 0 | 0 | 0 | 0 | 0 | 0 | 0 | 0 |
|  | 0.0078 | 0 | 0 | 0 | 0 | 0 | 0 | 0 | 0 |
| 41 | 0.25 | 50 | 90 | 0 | 25 | 50 | 40 | 0 | 0 |
|  | 0.0625 | 0 | 20 | 0 | 0 | 0 | 0 | 0 | 0 |
| 42 | 0.25 | 35 | 65 | 60 | 65 | 0 | 0 | 5 | 0 |
|  | 0.0625 | 30 | 0 | 0 | 0 | 0 | 0 | 5 | 0 |
| 43 | 0.25 | 15 | 65 | 10 | 45 | 35 | 15 | 0 | 0 |
|  | 0.0625 | 0 | 0 | 50 | 0 | 0 | 0 | 10 | 0 |
| 44 | 0.25 | 10 | 60 | 50 | 0 | 40 | 50 | 0 | 0 |
|  | 0.0625 | 55 | 0 | 30 | 0 | 10 | 5 | 0 | 0 |
| 45 | 0.25 | 75 | 98 | 30 | 50 | 98 | 100 | 0 | 0 |
|  | 0.0625 | 25 | 60 | 35 | 50 | 95 | 95 | 0 | 0 |
| 46 | 0.25 | 0 | 80 | 20 | 10 | 75 | 40 | 0 | 0 |
|  | 0.0625 | 0 | 20 | 0 | 0 | 55 | 35 | 0 | 0 |
| 47 | 0.25 | 75 | 50 | 70 | 0 | 50 | 75 | 0 | 0 |
|  | 0.0625 | 25 | 25 | 65 | 0 | 25 | 20 | 0 | 0 |
| 48 | 0.25 | 100 | 95 | 99 | 45 | 98 | 99 | 35 | 0 |
|  | 0.0625 | 85 | 65 | 40 | 20 | 65 | 60 | 3 | 0 |
| 49 | 0.25 | 75 | 0 | 40 | 0 | 45 | 10 | 0 | 0 |
|  | 0.0625 | 25 | 0 | 65 | 0 | 0 | 0 | 0 | 0 |
| 50 | 0.25 | 25 | 40 | 0 | 0 | 0 | 0 | 0 | 0 |
|  | 0.0625 | 0 | 0 | 15 | 0 | 0 | 0 | 0 | 0 |
| 51 | 0.25 | 50 | 90 | 15 | 0 | 80 | 90 | 8 | 3 |
|  | 0.0625 | 0 | 80 | 15 | 0 | 50 | 40 | 0 | 0 |
| 52 | 0.25 | 100 | 100 | 70 | 65 | 100 | 100 | 75 | 5 |
|  | 0.0625 | 100 | 100 | 100 | 45 | 99 | 100 | 45 | 0 |
| 53 | 0.25 | 85 | 85 | 80 | 15 | 75 | 9 | 5 | 0 |
|  | 0.0625 | 70 | 85 | 60 | 45 | 60 | 70 | 8 | 5 |
| 54 | 0.25 | 100 | 100 | 40 | 35 | 99 | 99 | 10 | 5 |
|  | 0.0625 | 75 | 85 | 70 | 0 | 75 | 80 | 0 | 0 |
| 55 | 0.25 | 30 | 85 | 10 | 30 | 95 | 100 | 0 | 0 |
|  | 0.0625 | 65 | 0 | 0 | 0 | 90 | 80 | 5 | 0 |
| 56 | 0.25 | 100 | 100 | 80 | 20 | 80 | 90 | 0 | 0 |
|  | 0.0625 | 40 | 100 | 80 | 25 | 35 | 55 | 3 | 0 |
| 57 | 0.25 | 50 | 90 | 90 | 10 | 15 | 10 | 0 | 0 |
|  | 0.0625 | 20 | 90 | 75 | 5 | 0 | 0 | 15 | 0 |
| 58 | 0.25 | 100 | 100 | 100 | 75 | 100 | 100 | 20 | 25 |
|  | 0.0625 | 99 | 85 | 55 | 10 | 85 | 90 | 3 | 15 |

TABLE 3a

PREEMERGENCE TESTS
% PLANT INHIBITION

| Cpd No. | Rate lb/A | G | H | I | DD |
|---|---|---|---|---|---|
| 1 | 4.5 | 15 | 0 | 0 | 10 |
|  | 0.893 | 0 | 0 | 0 | 0 |
|  | 0.1785 | 0 | 0 | 0 | 0 |
| 34 | 4.5 | 25 | 0 | 10 | 5 |
|  | 0.893 | 0 | 0 | 0 | 0 |
|  | 0.1785 | 0 | 0 | 0 | 0 |
| 35 | 4.5 | 80 | 95 | 100 | 10 |
|  | 0.893 | 35 | 35 | 100 | 0 |
|  | 0.1785 | 0 | 0 | 30 | 0 |
| 36 | 0.893 | 100 | 100 | 100 | 25 |
|  | 0.1785 | 75 | 0 | 100 | 10 |
|  | 0.0357 | 0 | 0 | 20 | 0 |
|  | 0.0071 | 0 | 0 | 0 | 0 |
|  | 0.893 | 50 | 30 | 100 | 10 |
|  | 0.1785 | 0 | 25 | 80 | 0 |
|  | 0.0357 | 0 | 70 | 0 | 0 |
|  | 0.0071 | 0 | 0 | 0 | 0 |
| 37 | 0.893 | 100 | 100 | 100 | 100 |
|  | 0.1786 | 100 | 90 | 100 | 70 |
|  | 0.0357 | 70 | 20 | 85 | 10 |
|  | 0.0071 | 0 | 0 | 0 | 0 |
| 38 | 0.893 | 20 | 100 | 100 | 0 |
|  | 0.1785 | 15 | 98 | 100 | 15 |
|  | 0.0357 | 0 | 90 | 100 | 0 |
|  | 0.0071 | 0 | 20 | 45 | 0 |
| 39 | 0.893 | 100 | 100 | 100 | 100 |
|  | 0.1785 | 100 | 100 | 100 | 80 |
|  | 0.0357 | 100 | 100 | 100 | 15 |
|  | 0.0071 | 10 | 85 | 25 | 0 |
| 40 | 4.5 | 100 | 90 | 100 | 70 |
|  | 0.893 | 20 | 0 | 30 | 0 |
|  | 0.1785 | 0 | 0 | 0 | 0 |
|  | 0.0357 | 0 | 0 | 0 | 0 |

TABLE 3b

PREEMERGENCE TESTS
% PLANT INHIBITION

| Cpd No. | Rate lb/A | G | H | I | O | T | U | V | EE | DD |
|---|---|---|---|---|---|---|---|---|---|---|
| 2 | 0.25 | 15 | 60 | 50 | 25 | 15 | 25 | 55 | 20 | 7 |
|  | 0.0625 | 5 | 60 | 25 | 10 | 5 | 10 | 15 | 5 | 0 |
|  | 0.0156 | 5 | 60 | 35 | 30 | 10 | 15 | 50 | 10 | 0 |
| 3 | 0.25 | 5 | 0 | 5 | 30 | 5 | 0 | 0 | 5 | 0 |
|  | 0.0625 | 0 | 0 | 0 | 0 | 0 | 0 | 10 | 0 | 0 |
|  | 0.0156 | 0 | 0 | 0 | 5 | 0 | 0 | 0 | 0 | 0 |
|  | 0.0039 | 0 | 0 | 0 | 5 | 0 | 0 | 5 | 0 | 0 |
| 7 | 1 | 40 | 15 | 35 | 50 | 10 | 35 | 15 | 0 | 8 |
|  | 0.25 | 0 | 0 | 5 | 0 | 0 | 0 | 0 | 0 | 0 |
|  | 0.0625 | 0 | 0 | 0 | 0 | 0 | 0 | 0 | 0 | 0 |
| 8 | 0.25 | 100 | 100 | 90 | 100 | 95 | 100 | 100 | 98 | 0 |
|  | 0.0625 | 100 | 100 | 35 | 100 | 45 | 75 | 100 | 65 | 0 |
|  | 0.0156 | 75 | 85 | 20 | 100 | 20 | 20 | 100 | 25 | 0 |
|  | 0.5 | 100 | 100 | 100 | 100 | 100 | 100 | ND | 100 | 30 |
|  | 0.25 | 100 | 100 | 100 | 100 | 100 | 100 | ND | 100 | 15 |
|  | 0.125 | 100 | 100 | 100 | 100 | 100 | 100 | ND | 100 | 0 |
|  | 0.0625 | 100 | 100 | 100 | 100 | 90 | 85 | ND | 85 | 0 |
|  | 0.0313 | 100 | 100 | 100 | 100 | 90 | 97 | ND | 50 | 0 |
|  | 0.0156 | 95 | 100 | 90 | 90 | 50 | 50 | ND | 50 | 0 |
|  | 0.0078 | 100 | 100 | 75 | 100 | 75 | 65 | ND | 60 | 0 |
|  | 0.5 | 100 | 100 | 100 | 100 | 100 | 100 | 100 | 95 | 10 |
|  | 0.25 | 100 | 100 | 100 | 100 | 100 | 99 | 100 | 90 | 0 |
|  | 0.125 | 100 | 100 | 100 | 100 | 97 | 95 | 100 | 90 | 0 |
|  | 0.0625 | 100 | 100 | 99 | 100 | 95 | 90 | 100 | 65 | 0 |
|  | 0.0313 | 100 | 99 | 65 | 100 | 85 | 75 | 100 | 45 | 0 |
|  | 0.0156 | 97 | 95 | 80 | 100 | 70 | 40 | 99 | 40 | 0 |
|  | 0.0078 | 88 | 75 | 65 | 100 | 30 | 30 | 97 | 20 | 0 |
|  | 0.0039 | 45 | 30 | 30 | 100 | 10 | 15 | 95 | 10 | 0 |
| 9 | 0.25 | 80 | 90 | 20 | 100 | 5 | 5 | 90 | 30 | 0 |
|  | 0.0625 | 40 | 20 | 5 | 100 | 0 | 0 | 90 | 25 | 0 |
|  | 0.0156 | 30 | 15 | 5 | 70 | 0 | 0 | 40 | 5 | 0 |
| 10 | 0.25 | 20 | 5 | 30 | 98 | 5 | 25 | 80 | 50 | 0 |
|  | 0.0625 | 5 | 0 | 5 | 60 | 0 | 0 | 65 | 5 | 0 |
|  | 0.0156 | 0 | 5 | 0 | 10 | 0 | 0 | 55 | 5 | 0 |
|  | 0.0039 | 0 | 0 | 0 | 15 | 0 | 0 | 65 | 10 | 0 |
| 11 | 0.25 | 60 | 25 | 75 | 100 | 20 | 10 | 95 | 15 | 0 |
|  | 0.0625 | 20 | 25 | 10 | 75 | 0 | 5 | 60 | 5 | 0 |
|  | 0.0156 | 25 | 15 | 5 | 10 | 0 | 5 | 65 | 5 | 0 |
|  | 0.0039 | 15 | 35 | 10 | 5 | 0 | 5 | 60 | 0 | 0 |
| 12 | 0.25 | 60 | 85 | 65 | 98 | 60 | 60 | 80 | 15 | 5 |
|  | 0.0625 | 55 | 75 | 60 | 98 | 40 | 35 | 80 | 10 | 0 |
|  | 0.0156 | 35 | 45 | 20 | 95 | 15 | 15 | 30 | 5 | 0 |
|  | 0.0039 | 25 | 15 | 10 | 70 | 5 | 5 | 35 | 0 | 0 |
| 13 | 0.25 | 98 | 90 | 100 | 100 | 95 | 100 | 90 | 65 | 3 |
|  | 0.0625 | 98 | 90 | 90 | 100 | 75 | 65 | 90 | 45 | 2 |
|  | 0.0156 | 65 | 25 | 50 | 100 | 25 | 25 | 30 | 10 | 0 |
|  | 0.0039 | 20 | 20 | 10 | 98 | 5 | 5 | 25 | 0 | 0 |
| 14 | 0.25 | 65 | 98 | 20 | 100 | 50 | 30 | 98 | 5 | 2 |
|  | 0.0625 | 25 | 80 | 5 | 85 | 5 | 5 | 25 | 0 | 0 |
|  | 0.0156 | 10 | 85 | 5 | 30 | 5 | 10 | 25 | 0 | 0 |
|  | 0.0039 | 5 | 85 | 0 | 50 | 5 | 5 | 5 | 5 | 0 |
| 15 | 0.25 | 100 | 100 | 98 | 100 | 90 | 100 | 100 | 60 | 0 |
|  | 0.0625 | 80 | 100 | 65 | 100 | 90 | 70 | 80 | 15 | 0 |
|  | 0.0156 | 30 | 90 | 10 | 100 | 40 | 15 | 35 | 10 | 0 |
|  | 0.0039 | 30 | 75 | 0 | 100 | 5 | 5 | 55 | 5 | 0 |
| 16 | 0.25 | 15 | 95 | 45 | 10 | 20 | 20 | 100 | 55 | 0 |
|  | 0.0625 | 10 | 95 | 45 | 15 | 10 | 25 | 95 | 85 | 0 |
|  | 0.0156 | 5 | 80 | 75 | 15 | 15 | 20 | 80 | 10 | 0 |
| 17 | 0.25 | 20 | 100 | 100 | 35 | 15 | 30 | 100 | 90 | 0 |
|  | 0.0625 | 15 | 70 | 55 | 20 | 10 | 25 | 98 | 45 | 0 |
|  | 0.0156 | 30 | 75 | 45 | 60 | 5 | 10 | 80 | 20 | 0 |
| 18 | 0.25 | 95 | 100 | 100 | 100 | 80 | 85 | 100 | 100 | 0 |
|  | 0.0625 | 70 | 65 | 50 | 100 | 25 | 15 | 98 | 55 | 0 |
|  | 0.0156 | 25 | 25 | 5 | 100 | 10 | 20 | 98 | 20 | 0 |
| 19 | 0.25 | 95 | 100 | 80 | 100 | 75 | 40 | 100 | 50 | 0 |
|  | 0.0625 | 80 | 85 | 35 | 100 | 25 | 35 | 100 | 25 | 0 |
|  | 0.0156 | 35 | 15 | 10 | 100 | 20 | 20 | 95 | 40 | 0 |
| 20 | 0.25 | 70 | 100 | 100 | 100 | 25 | 65 | 100 | 95 | 0 |
|  | 0.0625 | 25 | 98 | 75 | 100 | 20 | 25 | 100 | 45 | 0 |
|  | 0.0156 | 25 | 98 | 55 | 100 | 10 | 30 | 95 | 30 | 0 |
| 21 | 0.25 | 95 | 98 | 90 | 100 | 60 | 35 | 100 | 90 | 5 |
|  | 0.0625 | 65 | 80 | 60 | 90 | 5 | 10 | 70 | 20 | 0 |
|  | 0.0156 | 15 | 65 | 15 | 25 | 5 | 5 | 30 | 10 | 0 |

TABLE 3b-continued

PREEMERGENCE TESTS
% PLANT INHIBITION

| Cpd No. | Rate lb/A | G | H | I | O | T | U | V | EE | DD |
|---|---|---|---|---|---|---|---|---|---|---|
| 22 | 0.25 | 85 | 100 | 100 | 100 | 85 | 40 | 100 | 90 | 6 |
|  | 0.0625 | 40 | 60 | 45 | 85 | 20 | 10 | 100 | 15 | 5 |
|  | 0.0156 | 25 | 55 | 40 | 85 | 10 | 10 | 60 | 10 | 0 |
| 23 | 0.25 | 15 | 100 | 45 | 85 | 10 | 15 | 100 | 75 | 0 |
|  | 0.0625 | 35 | 25 | 15 | 100 | 5 | 20 | 50 | 15 | 0 |
|  | 0.0156 | 10 | 25 | 45 | 55 | 10 | 35 | 85 | 15 | 3 |
| 24 | 0.25 | 50 | 100 | 95 | 100 | 15 | 30 | 100 | 95 | 7 |
|  | 0.0625 | 25 | 70 | 35 | 15 | 5 | 10 | 40 | 20 | 0 |
|  | 0.0156 | 20 | 65 | 40 | 10 | 5 | 20 | 80 | 25 | 0 |
| 25 | 0.25 | 98 | 100 | 85 | 100 | 90 | 10 | 100 | 35 | 0 |
|  | 0.0625 | 90 | 90 | 35 | 98 | 25 | 10 | 85 | 35 | 0 |
|  | 0.0156 | 60 | 50 | 35 | 95 | 0 | 0 | 65 | 10 | 0 |
|  | 0.0039 | 55 | 25 | 0 | 80 | 0 | 0 | 25 | 5 | 0 |
| 26 | 0.25 | 95 | 100 | 80 | 100 | 65 | 55 | 100 | 40 | 0 |
|  | 0.0625 | 70 | 90 | 35 | 100 | 10 | 5 | 100 | 20 | 0 |
|  | 0.0156 | 20 | 60 | 15 | 100 | 0 | 0 | 80 | 15 | 0 |
|  | 0.0039 | 10 | 25 | 5 | 45 | 0 | 0 | 35 | 10 | 0 |
| 27 | 0.25 | 35 | 75 | 65 | 100 | 5 | 5 | 35 | 10 | 0 |
|  | 0.0625 | 15 | 35 | 35 | 70 | 0 | 5 | 30 | 5 | 0 |
|  | 0.0156 | 5 | 25 | 5 | 35 | 0 | 0 | 20 | 0 | 0 |
|  | 0.0039 | 10 | 15 | 0 | 25 | 0 | 0 | 65 | 0 | 0 |
| 28 | 0.25 | 30 | 25 | 40 | 90 | 0 | 0 | 70 | 5 | 0 |
|  | 0.0625 | 15 | 10 | 15 | 45 | 0 | 0 | 45 | 0 | 0 |
|  | 0.0156 | 15 | 5 | 5 | 40 | 0 | 0 | 45 | 0 | 0 |
|  | 0.0039 | 15 | 15 | 5 | 40 | 0 | 0 | 35 | 0 | 0 |
| 29 | 0.25 | 40 | 90 | 70 | 95 | 15 | 10 | 70 | 15 | 0 |
|  | 0.0625 | 10 | 30 | 40 | 50 | 0 | 5 | 65 | 0 | 0 |
|  | 0.0156 | 5 | 40 | 30 | 50 | 0 | 5 | 30 | 5 | 0 |
|  | 0.0039 | 5 | 0 | 5 | 35 | 0 | 5 | 55 | 5 | 0 |
| 30 | 0.25 | 20 | 35 | 40 | 98 | 0 | 5 | 50 | 5 | 0 |
|  | 0.0625 | 10 | 15 | 10 | 60 | 0 | 5 | 50 | 5 | 0 |
|  | 0.0156 | 5 | 20 | 5 | 35 | 0 | 5 | 15 | 0 | 0 |
|  | 0.0039 | 0 | 5 | 5 | 15 | 0 | 0 | 5 | 0 | 0 |
| 31 | 0.25 | 5 | 25 | 30 | 20 | 5 | 5 | 25 | 5 | 0 |
|  | 0.0625 | 5 | 20 | 15 | 5 | 0 | 0 | 20 | 5 | 0 |
|  | 0.0156 | 0 | 5 | 10 | 5 | 0 | 5 | 35 | 0 | 0 |
|  | 0.0039 | 0 | 5 | 0 | 5 | 0 | 0 | 15 | 0 | 0 |
| 32 | 0.25 | 10 | 5 | 5 | 40 | 0 | 0 | 45 | 5 | 0 |
|  | 0.0625 | 0 | 10 | 0 | 25 | 5 | 0 | 30 | 0 | 0 |
|  | 0.0156 | 0 | 35 | 2 | 50 | 0 | 0 | 55 | 5 | 0 |
|  | 0.0039 | 0 | 25 | 5 | 0 | 0 | 0 | 40 | 0 | 0 |
| 33 | 0.25 | 40 | 30 | 45 | 50 | 5 | 10 | 55 | 10 | 0 |
|  | 0.0625 | 10 | 20 | 20 | 10 | 0 | 5 | 20 | 5 | 0 |
|  | 0.0156 | 15 | 30 | 35 | 20 | 0 | 10 | 50 | 0 | 0 |
| 41 | 0.25 | 15 | 55 | 60 | 100 | 10 | 30 | 100 | 5 | 3 |
|  | 0.0625 | 10 | 20 | 35 | 98 | 5 | 10 | 95 | 0 | 0 |
| 42 | 0.25 | 15 | 40 | 80 | 95 | 5 | 10 | 30 | 5 | 0 |
|  | 0.0625 | 5 | 0 | 0 | 70 | 0 | 0 | 5 | 0 | 0 |
| 43 | 0.25 | 10 | 55 | 20 | 60 | 5 | 5 | 60 | 5 | 0 |
|  | 0.0625 | 5 | 5 | 0 | 20 | 0 | 5 | 5 | 0 | 0 |
| 44 | 0.25 | 20 | 85 | 40 | 100 | 5 | 5 | 85 | 20 | 0 |
|  | 0.0625 | 5 | 30 | 60 | 80 | 0 | 5 | 75 | 0 | 0 |
| 45 | 0.25 | 100 | 80 | 98 | 100 | 80 | 98 | 100 | 5 | 0 |
|  | 0.0625 | 30 | 35 | 50 | 100 | 20 | 45 | 98 | 0 | 0 |
| 46 | 0.25 | 10 | 90 | 75 | 80 | 5 | 15 | 80 | 5 | 0 |
|  | 0.0625 | 5 | 60 | 50 | 7 | 50 | 10 | 70 | 0 | 0 |
| 47 | 0.25 | 25 | 70 | 95 | 100 | 5 | 20 | 70 | 5 | 0 |
|  | 0.0625 | 15 | 10 | 45 | 85 | 0 | 10 | 10 | 5 | 0 |
| 48 | 0.25 | 60 | 95 | 45 | 100 | 45 | 90 | 100 | 5 | 0 |
|  | 0.0625 | 15 | 15 | 10 | 100 | 10 | 20 | 70 | 10 | 0 |
| 49 | 0.25 | 5 | 5 | 5 | 60 | 5 | 5 | 55 | 0 | 0 |
|  | 0.0625 | 5 | 0 | 5 | 30 | 0 | 5 | 40 | 0 | 0 |
| 50 | 0.25 | 5 | 35 | 25 | 10 | 0 | 5 | 35 | 0 | 0 |
|  | 0.0625 | 0 | 5 | 0 | 25 | 0 | 5 | 25 | 0 | 0 |
| 51 | 0.25 | 20 | 70 | 55 | 100 | 15 | 35 | 90 | 5 | 0 |
|  | 0.0625 | 10 | 10 | 5 | 100 | 5 | 5 | 55 | 5 | 0 |
| 52 | 0.25 | 100 | 95 | 90 | 100 | 85 | 100 | 95 | 60 | 0 |
|  | 0.0625 | 80 | 80 | 80 | 100 | 40 | 75 | 80 | 20 | 0 |
| 53 | 0.25 | 15 | 40 | 50 | 100 | 5 | 15 | 70 | 5 | 0 |
|  | 0.0625 | 35 | 10 | 90 | 100 | 10 | 25 | 80 | 10 | 0 |
| 54 | 0.25 | 35 | 90 | 80 | 100 | 30 | 75 | 98 | 0 | 5 |
|  | 0.0625 | 15 | 70 | 20 | 100 | 10 | 10 | 75 | 0 | 0 |
| 55 | 0.25 | 60 | 75 | 85 | 100 | 35 | 55 | 100 | 5 | 0 |

TABLE 3b-continued

PREEMERGENCE TESTS
% PLANT INHIBITION

| Cpd No. | Rate lb/A | G | H | I | O | T | U | V | EE | DD |
|---|---|---|---|---|---|---|---|---|---|---|
|  | 0.0625 | 15 | 15 | 0 | 95 | 0 | 15 | 75 | 0 | 0 |
| 56 | 0.25 | 75 | 95 | 90 | 100 | 55 | 100 | 100 | 5 | 5 |
|  | 0.0625 | 40 | 65 | 60 | 200 | 25 | 40 | 70 | 0 | 0 |
| 57 | 0.25 | 15 | 20 | 80 | 85 | 5 | 20 | 60 | 0 | 0 |
|  | 0.0625 | 5 | 5 | 5 | 50 | 0 | 5 | 5 | 0 | 0 |
| 58 | 0.25 | 95 | 100 | 95 | 100 | 75 | 100 | 100 | 50 | 5 |
|  | 0.0625 | 50 | 45 | 45 | 100 | 25 | 35 | 80 | 5 | 0 |

Post-Emergence Herbicide Tests

The post-emergence herbicidal activity of some of the various compounds of this invention was demonstrated by greenhouse testing in the following manner.

Topsoil was placed in aluminum pans having holes in the bottom and compacted to a depth of 1.3 to 1.6 cm from the top of the pan. A predetermined number of seeds of each of several dicotyledonous and monocotyledonous annual plant species and/or vegetative propagules for the perennial plant species were placed on the soil and pressed into the soil surface. The seeds and/or vegetative propagules were covered with soil and leveled. The pans were then placed on a bench in the greenhouse and watered either from overheard irrigation or by subirrigation as needed. After the plants reach the desired age (two to three weeks), each pan, is removed individually to a spraying chamber and sprayed by means of an atomizer, operating at a spray pressure of 170.3 kPa (10 psig) at the application rates noted. In the spray solution was an amount of an emulsifying agent mixture to give a spray solution or suspension which contains about 0.4% by volume of the emulsifier. The spray solution or suspension contained a sufficient amount of the candidate chemical in order to give application rates of the active ingredient corresponding to those shown in Tables 4 and 5, while applying a total amount of solution or suspension equivalent to 1870 L/Ha (200 gallons/acre). The pans were returned to the greenhouse and watered as before and the injury to the plants as compared to the control was observed at approximately 10–14 days (usually 11 days) and in some instances observed again at 24–28 days (usually 25 days) after spraying. The post-emergent herbicidal activity shown in these tables is the percent inhibition of each plant species. Testing with warm season and cool season plants is shown in tables 4a–4d and 3a–3b, respectively. Table subdivisions a through d represent different spectra of plants tested.

TABLE 4a

POSTEMERGENCE TESTS
% PLANT INHIBITION

| Cpd No. | Rate lb/A | A | B | C | D | E | F | G | BB | CC |
|---|---|---|---|---|---|---|---|---|---|---|
| 1 | 4.5 | 50 | 30 | 0 | 20 | 15 | 0 | 0 | 40 | 0 |
|  | 0.893 | 0 | 0 | 0 | 0 | 0 | 0 | 0 | 0 | 0 |
|  | 0.1785 | 0 | 0 | 0 | 0 | 0 | 0 | 0 | 0 | 0 |
| 34 | 4.5 | 0 | 0 | 10 | 20 | 55 | 25 | 0 | 15 | 15 |
|  | 0.893 | 0 | 0 | 0 | 0 | 0 | 0 | 0 | 0 | 10 |
|  | 0.1785 | 0 | 0 | 0 | 0 | 0 | 0 | 0 | 0 | 0 |
| 35 | 4.5 | 65 | 0 | 65 | 100 | 95 | 90 | 0 | 75 | 55 |
|  | 0.893 | 15 | 0 | 20 | 75 | 85 | 5 | 50 | 60 | 30 |
|  | 0.1785 | 0 | 0 | 0 | 50 | 65 | 0 | 0 | 30 | 20 |
|  | 0.893 | 35 | 0 | 0 | 70 | 100 | 15 | 0 | 25 | 55 |
|  | 0.1785 | 20 | 0 | 0 | 45 | 75 | 0 | 0 | 20 | 25 |
|  | 0.0357 | 0 | 0 | 0 | 0 | 0 | 0 | 0 | 0 | 0 |
|  | 0.0071 | 0 | 0 | 0 | 0 | 0 | 0 | 0 | 0 | 0 |
| 36 | 0.893 | 70 | 25 | 50 | 100 | 100 | 98 | 0 | 40 | 45 |
|  | 0.1785 | 45 | 0 | 45 | 75 | 85 | 60 | 0 | 30 | 35 |
|  | 0.0357 | 10 | 0 | 0 | 70 | 40 | 0 | 0 | 25 | 25 |
|  | 0.0071 | 0 | 0 | 0 | 65 | 20 | 75 | 0 | 0 | 15 |
| 37 | 0.893 | 65 | 40 | 45 | 100 | 100 | 80 | 15 | 100 | 60 |
|  | 0.1785 | 65 | 15 | 65 | 80 | 95 | 55 | 10 | 80 | 40 |
|  | 0.0357 | 20 | 10 | 15 | 35 | 45 | 40 | 0 | 10 | 40 |
|  | 0.0071 | 0 | 0 | 0 | 25 | 0 | 5 | 0 | 5 | 10 |
| 38 | 0.893 | 15 | 25 | 15 | 100 | 100 | 100 | 0 | 25 | 25 |
|  | 0.1785 | 10 | 25 | 15 | 100 | 100 | 80 | 10 | 25 | 30 |
|  | 0.0357 | 35 | 25 | 10 | 100 | 100 | 80 | 0 | 10 | 20 |
|  | 0.0071 | 0 | 35 | 10 | 65 | 80 | 80 | 0 | 5 | 10 |
| 39 | 0.893 | 100 | 30 | 98 | 100 | 95 | 100 | 70 | 95 | 100 |
|  | 0.1785 | 100 | 10 | 98 | 100 | 100 | 80 | 25 | 100 | 70 |
|  | 0.0357 | 100 | 40 | 70 | 100 | 80 | 98 | 35 | 30 | 70 |
|  | 0.0071 | 65 | 0 | 30 | 75 | 95 | 80 | 10 | 50 | 25 |
| 40 | 4.5 | 100 | 0 | 85 | 100 | 100 | 100 | 30 | 50 | 80 |

TABLE 4a-continued

POSTEMERGENCE TESTS
% PLANT INHIBITION

| Cpd No. | Rate lb/A | A | B | C | D | E | F | G | BB | CC |
|---|---|---|---|---|---|---|---|---|---|---|
| | 0.893 | 10 | 0 | 65 | 100 | 80 | 70 | 50 | 85 | 70 |
| | 0.1785 | 0 | 55 | 0 | 75 | 70 | 65 | 0 | 45 | 30 |
| | 0.0357 | 0 | 70 | 0 | 55 | 50 | 80 | 0 | 25 | 25 |

TABLE 4b

POSTEMERGENCE TESTS
% PLANT INHIBITION

| Cpd No. | Rate lb/A | C | D | E | F | P | BB | CC |
|---|---|---|---|---|---|---|---|---|
| 37 | 0.0625 | 50 | 55 | 60 | 50 | 45 | 45 | 70 |
| | 0.0313 | 40 | 40 | 40 | 40 | 45 | 35 | 45 |
| | 0.0156 | 35 | 40 | 40 | 40 | 40 | 35 | 30 |
| | 0.078 | 0 | 15 | 20 | 10 | 0 | 0 | 0 |
| | 0.0039 | 0 | 0 | 0 | 0 | 0 | 0 | 0 |

TABLE 4c

POSTEMERGENCE TESTS
% PLANT INHIBITION

| Cpd No. | Rate lb/A | D | E | F | N | Q | R | S | BB | CC |
|---|---|---|---|---|---|---|---|---|---|---|
| 38 | 0.25 | 100 | 95 | 100 | 50 | 20 | 100 | 100 | 10 | 15 |
| | 0.125 | 99 | 98 | 100 | 0 | 0 | 100 | 99 | 10 | 10 |
| | 0.0625 | 100 | 100 | 99 | 0 | 0 | 100 | 99 | 10 | 5 |
| | 0.0313 | 80 | 90 | 99 | 0 | 0 | 100 | 80 | 5 | 5 |
| | 0.0156 | 70 | 90 | 90 | 0 | 0 | 100 | 65 | 5 | 0 |
| | 0.078 | 65 | 85 | 70 | 0 | 0 | 100 | 70 | 5 | 0 |

TABLE 4d

POSTEMERGENCE TESTS
% PLANT INHIBITION

| Cpd No. | Rate lb/A | C | D | E | F | L | P | BB | CC |
|---|---|---|---|---|---|---|---|---|---|
| 2 | 0.25 | 15 | 85 | 45 | 70 | 20 | 0 | 3 | 20 |
| | 0.0625 | 0 | 45 | 15 | 65 | 0 | 0 | 2 | 10 |
| | 0.0156 | 0 | 10 | 5 | 15 | 0 | 0 | 0 | 5 |
| 3 | 0.25 | 0 | 85 | 25 | 65 | 0 | 0 | 2 | 15 |
| | 0.0625 | 0 | 10 | 0 | 15 | 0 | 0 | 0 | 3 |
| | 0.0156 | 0 | 0 | 0 | 0 | 0 | 0 | 0 | 0 |
| | 0.0039 | 0 | 0 | 0 | 0 | 0 | 0 | 0 | 0 |
| 7 | 1 | 0 | 25 | 20 | 5 | 30 | 0 | 0 | 20 |
| | 0.25 | 0 | 5 | 0 | 0 | 0 | 0 | 0 | 5 |
| | 0.0625 | 0 | 20 | 0 | 0 | 0 | 0 | 0 | 0 |
| 8 | 0.25 | 40 | 90 | 40 | 75 | 70 | 30 | 15 | 35 |
| | 0.0625 | 15 | 90 | 30 | 70 | 55 | 15 | 8 | 25 |
| | 0.0156 | 0 | 75 | 5 | 65 | 5 | 0 | 2 | 5 |
| | 0.25 | 85 | 99 | 95 | 99 | 90 | 80 | 20 | 75 |
| | 0.0625 | 30 | 90 | 60 | 75 | 35 | 35 | 8 | 25 |
| | 0.0156 | 5 | 70 | 65 | 45 | 15 | 5 | 5 | 15 |
| | 0.0039 | 0 | 50 | 55 | 40 | 0 | 0 | 2 | 10 |
| 9 | 0.25 | 25 | 95 | 45 | 35 | 20 | 10 | 10 | 60 |
| | 0.0625 | 10 | 80 | 20 | 25 | 5 | 0 | 5 | 15 |
| | 0.0156 | 0 | 65 | 15 | 5 | 20 | 5 | 2 | 20 |
| 10 | 0.25 | 5 | 90 | 35 | 55 | 15 | 15 | 3 | 8 |
| | 0.0625 | 0 | 75 | 15 | 40 | 5 | 5 | 2 | 7 |
| | 0.0156 | 0 | 35 | 5 | 25 | 0 | 0 | 0 | 5 |
| | 0.0039 | 0 | 25 | 0 | 0 | 0 | 0 | 0 | 0 |

TABLE 4d-continued

POSTEMERGENCE TESTS
% PLANT INHIBITION

| Cpd No. | Rate lb/A | C | D | E | F | L | P | BB | CC |
|---|---|---|---|---|---|---|---|---|---|
| 11 | 0.25 | 0 | 50 | 25 | 15 | 5 | 0 | 15 | 20 |
| | 0.0625 | 5 | 25 | 5 | 15 | 5 | 0 | 3 | 7 |
| | 0.0156 | 0 | 5 | 5 | 5 | 0 | 0 | 0 | 5 |
| | 0.0039 | 0 | 5 | 0 | 0 | 0 | 0 | 0 | 5 |
| 12 | 0.25 | 80 | 99 | 99 | 98 | 65 | 35 | 15 | 85 |
| | 0.0625 | 40 | 95 | 95 | 80 | 55 | 20 | 8 | 35 |
| | 0.0156 | 10 | 95 | 90 | 80 | 25 | 0 | 10 | 20 |
| | 0.0039 | 5 | 80 | 70 | 70 | 5 | 5 | 5 | 20 |
| 13 | 0.25 | 90 | 100 | 98 | 95 | 100 | 95 | 55 | 90 |
| | 0.0625 | 80 | 100 | 95 | 95 | 98 | 90 | 25 | 75 |
| | 0.0156 | 10 | 95 | 85 | 95 | 65 | 20 | 20 | 40 |
| | 0.0039 | 5 | 85 | 70 | 65 | 35 | 5 | 5 | 25 |
| 14 | 0.25 | 65 | 99 | 85 | 95 | 80 | 25 | 10 | 25 |
| | 0.0625 | 5 | 90 | 75 | 85 | 65 | 35 | 8 | 20 |
| | 0.0156 | 0 | 65 | 35 | 35 | 55 | 5 | 2 | 15 |
| | 0.0039 | 5 | 65 | 25 | 10 | 45 | 5 | 5 | 15 |
| 15 | 0.25 | 99 | 100 | 98 | 99 | 100 | 90 | 65 | 90 |
| | 0.0625 | 65 | 99 | 98 | 95 | 100 | 93 | 20 | 65 |
| | 0.0156 | 5 | 95 | 65 | 75 | 85 | 10 | 10 | 35 |
| | 0.0039 | 0 | 80 | 65 | 75 | 70 | 5 | 8 | 10 |
| 16 | 0.25 | 0 | 0 | 5 | 0 | 0 | 0 | 0 | 0 |
| | 0.0625 | 0 | 0 | 0 | 0 | 0 | 0 | 0 | 0 |
| | 0.0156 | 0 | 0 | 0 | 0 | 0 | 0 | 0 | 0 |
| 17 | 0.25 | 70 | 99 | 90 | 95 | 65 | 45 | 10 | 30 |
| | 0.0625 | 35 | 95 | 65 | 85 | 20 | 10 | 8 | 15 |
| | 0.0156 | 15 | 70 | 20 | 65 | 5 | 0 | 2 | 10 |
| 18 | 0.25 | 5 | 90 | 50 | 65 | 35 | 5 | 15 | 40 |
| | 0.0625 | 0 | 65 | 15 | 40 | 10 | 0 | 3 | 30 |
| | 0.0156 | 0 | 60 | 15 | 3 | 0 | 0 | 2 | 5 |
| 19 | 0.25 | 65 | 90 | 35 | 75 | 80 | 65 | 20 | 50 |
| | 0.0625 | 5 | 70 | 20 | 65 | 35 | 5 | 5 | 15 |
| | 0.0156 | 0 | 40 | 10 | 40 | 10 | 0 | 3 | 10 |
| 20 | 0.25 | 85 | 100 | 98 | 90 | 80 | 75 | 8 | 35 |
| | 0.0625 | 80 | 99 | 80 | 90 | 85 | 55 | 7 | 35 |
| | 0.0156 | 20 | 99 | 65 | 80 | 60 | 25 | 5 | 15 |
| 21 | 0.25 | 25 | 90 | 90 | 65 | 35 | 35 | 10 | 35 |
| | 0.0625 | 20 | 45 | 50 | 25 | 25 | 15 | 5 | 25 |
| | 0.0156 | 35 | 55 | 15 | 55 | 35 | 35 | 3 | 10 |
| 22 | 0.25 | 30 | 90 | 40 | 65 | 60 | 75 | 5 | 50 |
| | 0.0625 | 20 | 55 | 30 | 65 | 20 | 25 | 5 | 20 |
| | 0.0156 | 15 | 40 | 25 | 45 | 20 | 15 | 3 | 5 |
| 23 | 0.25 | 60 | 98 | 65 | 90 | 65 | 20 | 7 | 30 |
| | 0.0625 | 25 | 80 | 60 | 75 | 35 | 20 | 7 | 20 |
| | 0.0156 | 0 | 70 | 20 | 65 | 10 | 0 | 3 | 5 |
| 24 | 0.25 | 15 | 99 | 75 | 85 | 20 | 15 | 10 | 45 |
| | 0.0625 | 10 | 98 | 65 | 75 | 10 | 5 | 10 | 35 |
| | 0.0156 | 5 | 69 | 25 | 55 | 5 | 0 | 7 | 15 |
| 25 | 0.25 | 85 | 100 | 90 | 90 | 85 | 75 | 20 | 60 |
| | 0.0625 | 35 | 100 | 70 | 65 | 35 | 60 | 15 | 30 |
| | 0.0156 | 5 | 90 | 60 | 50 | 25 | 20 | 5 | 25 |
| | 0.0039 | 0 | 65 | 15 | 5 | 20 | 5 | 0 | 20 |
| 26 | 0.25 | 95 | 99 | 80 | 85 | 80 | 45 | 25 | 75 |
| | 0.0625 | 65 | 98 | 70 | 80 | 75 | 10 | 15 | 50 |
| | 0.0156 | 30 | 80 | 35 | 50 | 45 | 5 | 7 | 20 |
| | 0.0039 | 5 | 75 | 45 | 15 | 20 | 0 | 3 | 10 |
| 27 | 0.25 | 70 | 98 | 95 | 80 | 90 | 35 | 65 | 80 |
| | 0.0625 | 35 | 80 | 75 | 65 | 35 | 20 | 20 | 60 |

TABLE 4d-continued

POSTEMERGENCE TESTS
% PLANT INHIBITION

| Cpd No. | Rate lb/A | C | D | E | F | L | P | BB | CC |
|---|---|---|---|---|---|---|---|---|---|
| | 0.0156 | 5 | 65 | 75 | 35 | 35 | 5 | 20 | 25 |
| | 0.0039 | 5 | 10 | 35 | 15 | 15 | 0 | 15 | 20 |
| 28 | 0.25 | 10 | 60 | 65 | 40 | 20 | 25 | 40 | 20 |
| | 0.0625 | 0 | 25 | 20 | 20 | 35 | 5 | 20 | 15 |
| | 0.0156 | 0 | 20 | 15 | 25 | 20 | 0 | 5 | 15 |
| | 0.0039 | 0 | 15 | 15 | 15 | 10 | 5 | 20 | 35 |
| 29 | 0.25 | 90 | 99 | 90 | 90 | 90 | 65 | 20 | 90 |
| | 0.0625 | 40 | 95 | 65 | 75 | 70 | 55 | 8 | 80 |
| | 0.0156 | 5 | 95 | 75 | 70 | 25 | 5 | 5 | 35 |
| | 0.0039 | 15 | 70 | 45 | 45 | 20 | 0 | 5 | 20 |
| 30 | 0.25 | 60 | 85 | 65 | 60 | 70 | 20 | 20 | 65 |
| | 0.0625 | 15 | 70 | 35 | 50 | 35 | 20 | 8 | 30 |
| | 0.0156 | 5 | 65 | 5 | 20 | 10 | 5 | 5 | 15 |
| | 0.0039 | 5 | 35 | 0 | 15 | 0 | 0 | 3 | 15 |
| 31 | 0.25 | 70 | 99 | 80 | 99 | 90 | 50 | 50 | 35 |
| | 0.0625 | 50 | 98 | 65 | 80 | 75 | 40 | 50 | 15 |
| | 0.0156 | 35 | 85 | 35 | 75 | 20 | 0 | 7 | 10 |
| | 0.0039 | 20 | 75 | 25 | 65 | 10 | 0 | 2 | 7 |
| 32 | 0.25 | 35 | 85 | 40 | 65 | 45 | 45 | 15 | 20 |
| | 0.0625 | 15 | 65 | 20 | 45 | 25 | 25 | 3 | 15 |
| | 0.0156 | 0 | 25 | 0 | 15 | 15 | 15 | 2 | 7 |
| | 0.0039 | 0 | 10 | 0 | 10 | 0 | 0 | 2 | 5 |
| 33 | 0.25 | 0 | 10 | 10 | 0 | 0 | 0 | 0 | 15 |
| | 0.0625 | 0 | 0 | 5 | 0 | 0 | 0 | 0 | 5 |
| | 0.0156 | 0 | 15 | 5 | 0 | 0 | 0 | 0 | 0 |
| 41 | 0.25 | 65 | 99 | 75 | 95 | 70 | 5 | 35 | 15 |
| | 0.9625 | 15 | 98 | 70 | 85 | 55 | 15 | 5 | 10 |
| 42 | 0.25 | 65 | 98 | 70 | 85 | 45 | 0 | 25 | 10 |
| | 0.0625 | 10 | 98 | 40 | 60 | 35 | 0 | 5 | 7 |
| 43 | 0.25 | 5 | 80 | 75 | 85 | 25 | 0 | 7 | 15 |
| | 0.0625 | 5 | 65 | 15 | 70 | 10 | 0 | 10 | 5 |
| 44 | 0.25 | 90 | 99 | 80 | 99 | 60 | 65 | 15 | 10 |
| | 0.0625 | 15 | 90 | 75 | 90 | 25 | 0 | 3 | 8 |
| 45 | 0.25 | 75 | 100 | 80 | 100 | 95 | 80 | 55 | 35 |
| | 0.0625 | 55 | 100 | 90 | 85 | 80 | 35 | 10 | 20 |
| 46 | 0.25 | 50 | 98 | 70 | 85 | 25 | 0 | 15 | 15 |
| | 0.0625 | 10 | 90 | 35 | 75 | 15 | 0 | 15 | 7 |
| 47 | 0.25 | 5 | 100 | 70 | 100 | 50 | 5 | 50 | 30 |
| | 0.0625 | 20 | 90 | 40 | 80 | 25 | 5 | 5 | 8 |
| 48 | 0.25 | 60 | 100 | 75 | 90 | 85 | 99 | 7 | 70 |
| | 0.0625 | 45 | 99 | 80 | 80 | 90 | 95 | 7 | 45 |
| 49 | 0.25 | 0 | 10 | 5 | 50 | 5 | 0 | 5 | 5 |
| | 0.0625 | 0 | 25 | 0 | 30 | 0 | 0 | 5 | 5 |
| 50 | 0.25 | 5 | 90 | 35 | 60 | 0 | 0 | 5 | 7 |
| | 0.0625 | 5 | 40 | 5 | 50 | 0 | 0 | 3 | 7 |
| 51 | 0.25 | 60 | 100 | 35 | 85 | 85 | 85 | 7 | 65 |
| | 0.0625 | 30 | 99 | 30 | 75 | 20 | 45 | 5 | 45 |
| 52 | 0.25 | 99 | 100 | 99 | 100 | 99 | 100 | 15 | 95 |
| | 0.0625 | 55 | 100 | 85 | 99 | 100 | 99 | 10 | 65 |
| 53 | 0.25 | 70 | 100 | 99 | 100 | 75 | 75 | 7 | 75 |
| | 0.0625 | 25 | 95 | 50 | 75 | 25 | 15 | 5 | 40 |
| 54 | 0.25 | 95 | 100 | 80 | 99 | 90 | 90 | 35 | 80 |
| | 0.0625 | 65 | 99 | 50 | 85 | 70 | 35 | 7 | 20 |
| 55 | 0.25 | 45 | 99 | 85 | 90 | 70 | 35 | 20 | 20 |
| | 0.0625 | 20 | 90 | 35 | 65 | 15 | 0 | 10 | 15 |
| 56 | 0.25 | 80 | 100 | 80 | 99 | 95 | 100 | 35 | 90 |
| | 0.0625 | 60 | 99 | 95 | 95 | 85 | 90 | 7 | 65 |
| 57 | 0.25 | 35 | 100 | 50 | 85 | 35 | 15 | 3 | 17 |
| | 0.0625 | 15 | 90 | 35 | 70 | 20 | 5 | 2 | 20 |
| 58 | 0.25 | 85 | 100 | 100 | 99 | 95 | 95 | 20 | 85 |
| | 0.0625 | 65 | 100 | 85 | 99 | 90 | 90 | 5 | 45 |

TABLE 5a

POSTEMERGENCE TESTS
% PLANT INHIBITION

| Cpd No. | Rate lb/A | G | H | I | DD |
|---|---|---|---|---|---|
| 1 | 4.5 | 35 | 40 | 30 | 10 |
| | 0.893 | 0 | 0 | 0 | 0 |
| | 0.1785 | 0 | 0 | 0 | 0 |
| 34 | 4.5 | 30 | 0 | 80 | 10 |
| | 0.893 | 0 | 0 | 0 | 0 |
| | 0.1785 | 0 | 0 | 0 | 0 |
| 35 | 4.5000 | 45 | 35 | 85 | 25 |
| | 0.8930 | 35 | 10 | 75 | 20 |
| | 0.1785 | 0 | 0 | 0 | 0 |
| | 0.8930 | 35 | 0 | 95 | 15 |
| | 0.1785 | 15 | 0 | 75 | 5 |
| | 0.0357 | 0 | 0 | 25 | 0 |
| | 0.0071 | 0 | 0 | 0 | 0 |
| 36 | 0.8930 | 60 | 65 | 75 | 25 |
| | 0.1785 | 25 | 35 | 50 | 20 |
| | 0.0357 | 10 | 15 | 25 | 5 |
| | 0.0071 | 0 | 85 | 0 | 10 |
| 37 | 0.8930 | 85 | 80 | 90 | 30 |
| | 0.1785 | 65 | 70 | 75 | 10 |
| | 0.0357 | 25 | 40 | 35 | 0 |
| | 0.0071 | 10 | 0 | 20 | 5 |
| 38 | 0.8930 | 5 | 98 | 85 | 10 |
| | 0.1785 | 30 | 95 | 90 | 10 |
| | 0.0357 | 25 | 75 | 85 | 10 |
| | 0.0071 | 0 | 65 | 35 | 10 |
| 39 | 0.8930 | 100 | 100 | 100 | 75 |
| | 0.1785 | 95 | 100 | 100 | 15 |
| | 0.0357 | 80 | 100 | 100 | 0 |
| | 0.0071 | 0 | 0 | 0 | 0 |
| 40 | 4.5000 | 100 | 98 | 100 | 25 |
| | 0.8930 | 65 | 98 | 98 | 20 |
| | 0.1785 | 35 | 80 | 60 | 15 |
| | 0.0357 | 0 | 15 | 20 | 0 |

TABLE 5b

POSTEMERGENCE TESTS
% PLANT INHIBITION

| Cpd No. | Rate 1b/A | G | H | I | O | T | U | V | EE | DD |
|---|---|---|---|---|---|---|---|---|---|---|
| 2 | 0.25 | 10 | 70 | 50 | 15 | 0 | 0 | 80 | 0 | 0 |
|   | 0.0625 | 0 | 20 | 15 | 0 | 0 | 0 | 65 | 0 | 0 |
|   | 0.0156 | 0 | 0 | 0 | 0 | 0 | 0 | 50 | 0 | 0 |
| 3 | 0.25 | 0 | 25 | 15 | 10 | 5 | 0 | 75 | 10 | 8 |
|   | 0.0625 | 0 | 5 | 5 | 0 | 0 | 0 | 65 | 5 | 0 |
|   | 0.0156 | 0 | 5 | 5 | 0 | 0 | 0 | 15 | 5 | 0 |
|   | 0.0039 | 0 | 5 | 5 | 5 | 0 | 0 | 25 | 0 | 0 |
| 7 | 1 | 15 | 5 | 80 | 55 | 20 | 25 | 75 | 5 | 17 |
|   | 0.25 | 5 | 0 | 35 | 20 | 5 | 5 | 65 | 0 | 5 |
|   | 0.0625 | 0 | 0 | 5 | 5 | 0 | 0 | 60 | 5 | 0 |
| 8 | 0.25 | 5 | 40 | 60 | 20 | 25 | 30 | 55 | 25 | 12 |
|   | 0.0625 | 20 | 25 | 35 | 15 | 20 | 20 | 45 | 5 | 6 |
|   | 0.0156 | 10 | 25 | 20 | 10 | 15 | 10 | 35 | 5 | 5 |
|   | 0.25 | 85 | 100 | 95 | 90 | 80 | 85 | 100 | 65 | 40 |
|   | 0.125 | 55 | 80 | 90 | 90 | 75 | 60 | 95 | 65 | 20 |
|   | 0.0625 | 70 | 85 | 85 | 65 | 60 | 50 | 85 | 30 | 10 |
|   | 0.0313 | 25 | 15 | 70 | 50 | 30 | 40 | 50 | 10 | 5 |
|   | 0.0156 | 40 | 10 | 65 | 40 | 20 | 15 | 45 | 5 | 5 |
|   | 0.0078 | 25 | 5 | 60 | 55 | 10 | 15 | 40 | 15 | 7 |
|   | 0.5 | 98 | 100 | 98 | 100 | 98 | 98 | 100 | 100 | 75 |
|   | 0.25 | 97 | 100 | 95 | 97 | 97 | 97 | 100 | 100 | 60 |
|   | 0.125 | 93 | 88 | 80 | 95 | 75 | 70 | 99 | 97 | 40 |
|   | 0.0625 | 90 | 80 | 70 | 80 | 70 | 60 | 99 | 95 | 30 |
|   | 0.0313 | 70 | 95 | 65 | 45 | 40 | 40 | 85 | 65 | 25 |
|   | 0.0156 | 75 | 65 | 55 | 50 | 30 | 35 | 70 | 75 | 18 |
|   | 0.0078 | 50 | 50 | 40 | 35 | 15 | 10 | 50 | 15 | 12 |
|   | 0.0039 | 45 | 75 | 45 | 30 | 5 | 10 | 55 | 20 | 10 |
| 9 | 0.25 | 20 | 15 | 50 | 20 | 25 | 25 | 35 | 20 | 13 |
|   | 0.0625 | 10 | 10 | 20 | 15 | 10 | 10 | 10 | 5 | 5 |
|   | 0.0156 | 5 | 15 | 15 | 15 | 5 | 5 | 10 | 0 | 0 |
| 10 | 0.25 | 20 | 15 | 25 | 50 | 10 | 25 | 90 | 35 | 10 |
|   | 0.0625 | 10 | 5 | 15 | 40 | 10 | 15 | 55 | 15 | 7 |
|   | 0.0156 | 5 | 5 | 10 | 10 | 0 | 5 | 40 | 5 | 0 |
|   | 0.0039 | 0 | 5 | 5 | 5 | 0 | 5 | 25 | 0 | 0 |
| 11 | 0.25 | 15 | 10 | 50 | 25 | 5 | 10 | 60 | 5 | 6 |
|   | 0.0625 | 5 | 0 | 50 | 20 | 0 | 5 | 25 | 0 | 0 |
|   | 0.0156 | 0 | 0 | 5 | 5 | 0 | 0 | 10 | 5 | 0 |
|   | 0.0039 | 0 | 0 | 5 | 0 | 0 | 0 | 5 | 5 | 0 |
| 12 | 0.25 | 50 | 100 | 95 | 90 | 85 | 90 | 100 | 100 | 30 |
|   | 0.0625 | 25 | 98 | 65 | 70 | 60 | 70 | 100 | 100 | 25 |
|   | 0.0156 | 20 | 80 | 50 | 45 | 40 | 45 | 98 | 75 | 23 |
|   | 0.0039 | 15 | 70 | 35 | 20 | 35 | 35 | 100 | 70 | 22 |
| 13 | 0.25 | 95 | 98 | 100 | 100 | 90 | 90 | 100 | 100 | 20 |
|   | 0.0625 | 65 | 90 | 98 | 95 | 75 | 75 | 100 | 98 | 15 |
|   | 0.0156 | 20 | 70 | 75 | 75 | 40 | 35 | 100 | 80 | 14 |
|   | 0.0039 | 25 | 40 | 55 | 30 | 30 | 30 | 90 | 55 | 8 |
| 14 | 0.25 | 60 | 45 | 40 | 65 | 50 | 60 | 90 | 75 | 13 |
|   | 0.0625 | 30 | 40 | 25 | 25 | 25 | 35 | 90 | 40 | 10 |
|   | 0.0156 | 5 | 15 | 10 | 10 | 20 | 25 | 30 | 25 | 8 |
|   | 0.0039 | 5 | 5 | 5 | 5 | 5 | 10 | 20 | 10 | 0 |
| 15 | 0.25 | 100 | 100 | 100 | 100 | 100 | 100 | 100 | 100 | 20 |
|   | 0.0625 | 95 | 80 | 75 | 85 | 80 | 75 | 100 | 80 | 15 |
|   | 0.0156 | 50 | 65 | 75 | 50 | 40 | 40 | 100 | 45 | 10 |
|   | 0.0039 | 20 | 20 | 20 | 30 | 20 | 25 | 70 | 30 | 5 |
| 16 | 0.25 | 5 | 50 | 25 | 0 | 0 | 0 | 30 | 0 | 0 |
|   | 0.0625 | 5 | 10 | 5 | 0 | 0 | 0 | 10 | 0 | 0 |
|   | 0.0156 | 5 | 5 | 5 | 0 | 0 | 0 | 15 | 0 | 0 |
| 17 | 0.25 | 15 | 90 | 95 | 20 | 20 | 30 | 98 | 20 | 15 |
|   | 0.0625 | 10 | 75 | 70 | 15 | 20 | 25 | 100 | 15 | 10 |
|   | 0.0156 | 5 | 45 | 50 | 10 | 15 | 15 | 50 | 10 | 5 |
| 18 | 0.25 | 20 | 35 | 65 | 20 | 20 | 25 | 60 | 15 | 7 |
|   | 0.0625 | 10 | 30 | 55 | 15 | 15 | 15 | 40 | 10 | 5 |
|   | 0.0156 | 5 | 25 | 40 | 5 | 15 | 10 | 20 | 5 | 0 |
| 19 | 0.25 | 20 | 50 | 60 | 20 | 20 | 25 | 55 | 15 | 10 |
|   | 0.0625 | 15 | 10 | 45 | 15 | 20 | 20 | 35 | 5 | 5 |
|   | 0.0156 | 10 | 5 | 35 | 15 | 15 | 10 | 30 | 10 | 5 |
| 20 | 0.25 | 35 | 98 | 95 | 25 | 45 | 40 | 100 | 25 | 22 |
|   | 0.0625 | 25 | 80 | 55 | 20 | 30 | 35 | 98 | 20 | 18 |
|   | 0.0156 | 15 | 40 | 50 | 15 | 20 | 25 | 35 | 10 | 12 |
| 21 | 0.25 | 10 | 30 | 65 | 25 | 20 | 25 | 50 | 20 | 5 |
|   | 0.0625 | 5 | 15 | 35 | 15 | 5 | 15 | 25 | 15 | 0 |
|   | 0.0156 | 5 | 10 | 20 | 15 | 5 | 5 | 5 | 5 | 0 |
| 22 | 0.25 | 5 | 40 | 45 | 20 | 10 | 15 | 40 | 10 | 0 |

TABLE 5b-continued

POSTEMERGENCE TESTS
% PLANT INHIBITION

| Cpd No. | Rate lb/A | G | H | I | O | T | U | V | EE | DD |
|---|---|---|---|---|---|---|---|---|---|---|
| | 0.0625 | 5 | 35 | 40 | 15 | 5 | 15 | 35 | 0 | 0 |
| | 0.0156 | 0 | 20 | 25 | 10 | 5 | 5 | 20 | 10 | 0 |
| 23 | 0.25 | 15 | 75 | 50 | 15 | 20 | 25 | 75 | 10 | 11 |
| | 0.0625 | 10 | 65 | 50 | 15 | 20 | 15 | 45 | 5 | 7 |
| | 0.0156 | 5 | 30 | 25 | 10 | 10 | 5 | 25 | 5 | 0 |
| 24 | 0.25 | 25 | 90 | 65 | 20 | 25 | 25 | 95 | 25 | 20 |
| | 0.0625 | 20 | 70 | 70 | 20 | 20 | 25 | 80 | 10 | 19 |
| | 0.0156 | 5 | 35 | 55 | 15 | 15 | 20 | 75 | 5 | 7 |
| 25 | 0.25 | 40 | 90 | 65 | 65 | 35 | 50 | 95 | 40 | 16 |
| | 0.0625 | 30 | 40 | 60 | 35 | 25 | 25 | 40 | 25 | 7 |
| | 0.0156 | 15 | 15 | 50 | 25 | 10 | 15 | 15 | 0 | 5 |
| | 0.0039 | 5 | 10 | 10 | 15 | 5 | 10 | 10 | 5 | 0 |
| 26 | 0.25 | 35 | 85 | 60 | 60 | 35 | 45 | 85 | 60 | 17 |
| | 0.0625 | 25 | 55 | 55 | 30 | 25 | 40 | 50 | 25 | 10 |
| | 0.0156 | 0 | 25 | 40 | 5 | 10 | 15 | 15 | 15 | 0 |
| | 0.0039 | 0 | 0 | 5 | 5 | 0 | 0 | 10 | 5 | 0 |
| 27 | 0.25 | 30 | 65 | 90 | 75 | 25 | 40 | 100 | 80 | 13 |
| | 0.0625 | 20 | 40 | 75 | 50 | 15 | 35 | 90 | 50 | 10 |
| | 0.0156 | 10 | 25 | 35 | 35 | 5 | 25 | 70 | 30 | 8 |
| | 0.0039 | 10 | 25 | 25 | 30 | 10 | 15 | 75 | 25 | 7 |
| 28 | 0.25 | 10 | 25 | 60 | 50 | 15 | 20 | 85 | 20 | 8 |
| | 0.0625 | 5 | 15 | 20 | 45 | 5 | 10 | 75 | 20 | 5 |
| | 0.0156 | 5 | 5 | 10 | 10 | 5 | 5 | 40 | 15 | 0 |
| | 0.0039 | 5 | 10 | 10 | 15 | 5 | 5 | 50 | 10 | 3 |
| 29 | 0.25 | 70 | 95 | 100 | 95 | 75 | 70 | 100 | 100 | 12 |
| | 0.0625 | 50 | 90 | 65 | 70 | 60 | 60 | 95 | 100 | 8 |
| | 0.0156 | 15 | 70 | 40 | 25 | 35 | 45 | 85 | 60 | 7 |
| | 0.0039 | 5 | 25 | 20 | 20 | 15 | 20 | 75 | 35 | 5 |
| 30 | 0.25 | 30 | 75 | 40 | 65 | 25 | 25 | 98 | 60 | 15 |
| | 0.0625 | 15 | 40 | 30 | 40 | 20 | 20 | 70 | 40 | 16 |
| | 0.0156 | 10 | 20 | 25 | 35 | 15 | 20 | 50 | 25 | 8 |
| | 0.0039 | 10 | 20 | 25 | 20 | 15 | 20 | 40 | 15 | 6 |
| 31 | 0.25 | 20 | 95 | 70 | 75 | 35 | 55 | 100 | 75 | 20 |
| | 0.0625 | 15 | 75 | 60 | 60 | 25 | 40 | 100 | 60 | 17 |
| | 0.0156 | 10 | 60 | 40 | 20 | 20 | 30 | 70 | 20 | 16 |
| | 0.0039 | 10 | 50 | 40 | 15 | 20 | 35 | 75 | 15 | 14 |
| 32 | 0.25 | 25 | 20 | 45 | 65 | 20 | 25 | 90 | 50 | 15 |
| | 0.0625 | 15 | 15 | 35 | 25 | 15 | 20 | 80 | 25 | 10 |
| | 0.0156 | 5 | 10 | 10 | 10 | 5 | 5 | 20 | 10 | 5 |
| | 0.0039 | 5 | 15 | 10 | 10 | 5 | 10 | 40 | 5 | 5 |
| 33 | 0.25 | 5 | 10 | 10 | 15 | 5 | 5 | 15 | 5 | 5 |
| | 0.0625 | 5 | 5 | 5 | 5 | 0 | 5 | 5 | 5 | 0 |
| | 0.0156 | 0 | 10 | 5 | 5 | 0 | 5 | 5 | 0 | 0 |
| 41 | 0.25 | 20 | 98 | 100 | 90 | 20 | 30 | 100 | 40 | 15 |
| | 0.0625 | 15 | 90 | 50 | 60 | 20 | 20 | 98 | 25 | 10 |
| 42 | 0.25 | 20 | 95 | 100 | 40 | 20 | 30 | 95 | 40 | 15 |
| | 0.0625 | 15 | 65 | 90 | 30 | 15 | 20 | 75 | 15 | 5 |
| 43 | 0.25 | 10 | 65 | 30 | 20 | 15 | 10 | 100 | 25 | 10 |
| | 0.0625 | 5 | 30 | 25 | 20 | 10 | 10 | 70 | 15 | 5 |
| 44 | 0.25 | 25 | 95 | 100 | 90 | 25 | 35 | 100 | 45 | 15 |
| | 0.0625 | 15 | 60 | 50 | 35 | 20 | 20 | 90 | 25 | 15 |
| 45 | 0.25 | 98 | 100 | 100 | 100 | 80 | 95 | 100 | 50 | 17 |
| | 0.0625 | 35 | 70 | 70 | 60 | 35 | 50 | 100 | 25 | 15 |
| 46 | 0.25 | 20 | 95 | 100 | 70 | 20 | 15 | 100 | 45 | 15 |
| | 0.0625 | 10 | 60 | 65 | 45 | 20 | 5 | 80 | 25 | 10 |
| 47 | 0.25 | 20 | 95 | 90 | 70 | 30 | 20 | 95 | 65 | 15 |
| | 0.0625 | 15 | 90 | 35 | 55 | 25 | 15 | 98 | 40 | 10 |
| 48 | 0.25 | 70 | 65 | 80 | 98 | 75 | 65 | 100 | 60 | 16 |
| | 0.0625 | 25 | 35 | 30 | 80 | 35 | 35 | 90 | 15 | 10 |
| 49 | 0.25 | 20 | 10 | 35 | 60 | 20 | 20 | 80 | 20 | 10 |
| | 0.0625 | 5 | 5 | 30 | 45 | 10 | 10 | 70 | 10 | 5 |
| 50 | 0.25 | 5 | 60 | 35 | 25 | 10 | 10 | 75 | 15 | 10 |
| | 0.0625 | 5 | 15 | 35 | 15 | 10 | 10 | 50 | 10 | 10 |
| 51 | 0.25 | 45 | 75 | 40 | 80 | 55 | 45 | 98 | 20 | 12 |
| | 0.0625 | 25 | 95 | 40 | 45 | 30 | 45 | 70 | 20 | 7 |
| 52 | 0.25 | 95 | 100 | 100 | 98 | 95 | 100 | 100 | 100 | 25 |
| | 0.0625 | 65 | 95 | 95 | 95 | 80 | 90 | 100 | 98 | 15 |
| 53 | 0.25 | 25 | 90 | 95 | 80 | 40 | 45 | 95 | 98 | 16 |
| | 0.0625 | 20 | 75 | 90 | 40 | 20 | 20 | 70 | 60 | 12 |
| 54 | 0.25 | 30 | 90 | 98 | 98 | 80 | 70 | 100 | 75 | 16 |
| | 0.0625 | 25 | 90 | 100 | 70 | 45 | 75 | 90 | 25 | 15 |
| 55 | 0.25 | 20 | 70 | 75 | 65 | 30 | 20 | 95 | 15 | 10 |
| | 0.0625 | 60 | 90 | 80 | 100 | 70 | 70 | 100 | 45 | 15 |

TABLE 5b-continued

POSTEMERGENCE TESTS
% PLANT INHIBITION

| Cpd No. | Rate lb/A | G | H | I | O | T | U | V | EE | DD |
|---|---|---|---|---|---|---|---|---|---|---|
| 56 | 0.25 | 60 | 90 | 98 | 98 | 80 | 85 | 100 | 98 | 16 |
|  | 0.0625 | 35 | 90 | 85 | 75 | 40 | 55 | 90 | 70 | 15 |
| 57 | 0.25 | 15 | 55 | 40 | 40 | 25 | 15 | 100 | 15 | 8 |
|  | 0.0625 | 15 | 30 | 35 | 10 | 10 | 10 | 20 | 10 | 5 |
| 58 | 0.25 | 80 | 95 | 90 | 85 | 85 | 85 | 100 | 65 | 18 |
|  | 0.0625 | 40 | 90 | 65 | 80 | 50 | 40 | 100 | 50 | 15 |

The herbicidal compositions of this invention, including concentrates which require dilution prior to application, may contain at least one active ingredient and an adjuvant in liquid or solid form. The compositions are prepared by admixing the active ingredient with an adjuvant including diluents, extenders, carriers, and conditioning agents to provide compositions in the form of finely-divided particulate solids, granules, pellets, solutions, dispersions or emulsions. Thus, it is believed that the active ingredient could be used with an adjuvant such as a finely-divided solid, a liquid of organic origin, water, a wetting agent, a dispersing agent, an emulsifying agent or any suitable combination of these.

Suitable wetting agents are believed to include alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin sulfonates, polymeric alkyl naphthalene sulfonates, sodium naphthalene sulfonate, and polymethylene bisnaphthalene sulfonate. Wettable powders are water-dispersible compositions containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The wettable powders compositions of this invention usually contain from above 0.5 to 60 parts (preferably from 5-20 parts) of active ingredient, from about 0.25 to 25 parts (preferably 1-15 parts) of wetting agent, from about 0.25 to 25 parts (preferably 1.0-15 parts) of dispersant and from 5 to about 95 parts (preferably 5-50 parts) of inert solid extender, all parts being by weight of the total composition. Where required, from about 0.1 to 2.0 parts of the solid inert extender can be replaced by a corrosion inhibitor or antifoaming agent or both.

Other formulations include dust concentrates comprising from 0.1 to 60% by weight of the active ingredient on a suitable extender; these dusts may be diluted for application at concentrations within the range of from about 0.1-10% by weight.

Aqueous suspensions or emulsions may be prepared by stirring a nonaqueous solution of a water-insoluble active ingredient and an emulsification agent with water until uniform and then homogenizing to give stable emulsion of very finely divided particles. The resulting concentrated aqueous suspension is characterized by its extremely small particle size, so that when diluted and sprayed, coverage is very uniform. Suitable concentrations of these formulations contain from about 0.1–60%, preferably 5–50% by weight of active ingredient, the upper limit being determined by the solubility limit of active ingredient in the solvent. Concentrates are usually solutions of active ingredient in water-immiscible or partially water-immiscible solvents together with a surface active agent. Suitable solvents for the active ingredient of this invention include dimethylformamide, dimethylsulfoxide, N-methyl-pyrrolidone, hydrocarbons, and water-immiscible ethers, esters, or ketones. However, other high strength liquid concentrates may be formulated by dissolving the active ingredient in a solvent then diluting, e.g., with kerosene, to spray concentration.

The concentrate compositions herein generally contain from about 0.1 to 95 parts (preferably 5–60 parts) active ingredient, about 0.25 to 50 parts (preferably 1–25 parts) surface active agent and where required about 5 to 94 parts solvent, all parts being be weight based on the total weight of emulsifiable oil.

Granules are physically stable particulate compositions comprising active ingredient adhering to or distributed through a basic matrix of an inert, finely-divided particulate extender. In order to aid leaching of the active ingredient from the particulate extender, a surface active agent can be present in the composition. Natural clays, pyrophyllites, illite, and vermiculite are examples of operable classes of particulate mineral extenders. The preferred extenders are the porous, absorptive preformed particles such as preformed and screened particulate attapulgite or heat expanded, particulate vermiculite and the finely-divided clays such as kaolin clays, hydrated attapulgite or bentonitic clays. These extenders are sprayed or blended with the active ingredient to form the herbicidal granules.

The granular compositions of this invention may contain from about 0.1 to about 30 parts by weight of active ingredient per 100 parts by weight of clay and 0 to about 5 parts by weight of surface active agent per 100 parts by weight of particulate clay.

The compositions of this invention can also contain other additaments, for example, fertilizers, other herbicides, other pesticides, safeners and the like used as adjuvants or in combination with any of the above-described adjuvants. Chemicals useful in combination with the active ingredients of this invention included, for example, triazines, ureas, sulfonylureas, carbamates, acetamides, acetanilides, uracils, acetic acid or phenol derivatives, thiol- carbamates, triazoles, azolopyrimidines, benzoic acid and its derivatives, nitriles, biphenyl ethers, nitrobenzenes and the like such as:
Heterocyclic Nitrogen/Sulfur Derivatives
2-Chloro-4-ethylamino-6-isopropylamino-s-triazine 2-Chloro-4,6-bis(isopropylamino)-s-triazine
2-Chloro-4,6-bis(ethylamino)-s-triazine
3-Isopropyl-1H-2,1,3-benzothiadiazin-4-(3H)-one 2,2-dioxide
3-Amino-1,2,4-triazole
6,7-Dihydrodipyrido(1,2-:2',1'-c)-pyrazidiinium salt
5-Bromo-3-isopropyl-6-methyluracil
1,1'-Dimethyl-4,4'-bypyridinium
2-(4-Isopropyl-4-methyl-5-oxo-2-imidazolin-2-yl)-3-quinolinecarboxylic acid
Isopropylamine salt of 2-(4-isopropyl-4-methyl-5-oxo-2-imidazolin-2-yl)nicotinic acid
Methyl 6-(4-isopropyl-4-methyl-5-oxo-2-imidazolin-2-yl)-m-toluate and methyl 2-(4-isopropyl-4-methyl- 5-oxo-2-imidazolin-2-yl)-p-toluate
Ureas/Sulfonylureas
N-(4-Chlorophenoxy) phenyl-N,N-dimethylurea
N,N-dimethyl-N'-(3-chloro-4-methylphenyl) urea
3-(3,4-dichlorophenyl)-1,1-dimethylurea
1,3-Dimethyl-3-(2-benzothiazolyl) urea
3-(p-Chlorophenyl)-1,1-dimethylurea
1-Butyl-3-(3,4-dichlorophenyl)-1-methylurea
2-Chloro-N[(4-methoxy-6-methyl-1,3,5-triazin-2-yl) aminocarbonyl]-benzenesulfonamide
N-(2-methoxycarbonylphenyl sulfonyl()-N'-(4,6-bis-difluoromethoxypyrimidin-2-yl)urea
Methyl 2-(((((4,6-dimethyl-2-pyrimidinyl)amino)-carbonyl)amino)sulfonyl) benzoate
Ethyl 1-[methyl 2-(((((4,6-dimethyl-2-pyrimidinyl)-amino) carbonyl) amino)sulfonyl)] benzoate
Methyl-2((4,6-dimethoxy pyrimidin-2-yl) aminocarbonyl amino sulfonyl methyl) benzoate
Methyl 2-(((((4-methoxy-6-methyl-1,3,5-triazin-2-yl)-amino)carbonyl)amino)sulfonyl) benzoate
Carbamates/Thiolcarbamates
2-Chloroallyl diethyldithiocarbamate
S-(4-chlorobenzyl)N,N-diethylthiolcarbamate
Isopropyl N-(3-chlorophenyl) carbamate
S-2,3-dichloroallyl N,N-diisopropylthiolcarbamate
S-N,N-dipropylthiolcarbamate
S-propyl N,N-dipropylthiolcarbamate
S-2,3,3-trichloroallyl-N,N-diisopropylthiolcarbamate
Acetamides/Acetanilides/Anilines/Amides
2-Chloro-N,N-diallylacetamide
N,N-dimethyl-2,2-diphenylacetamide
N-(2,4-dimethylthien-3-yl)-N-(1-methoxyprop-2-yl)-2-chloroacetamide
N-(1H-pyrazol-1-ylmethyl-N-(2,4-dimethylthien-3-yl)-2-chloroacetamide
N-(1-pyrazol-1-ylmethyl)-N-(4,6-dimethoxypyrimidin-5-yl)-2-chloroacetamide
N-(2,4-dimethyl-5-[[[(trifluoromethyl) sulfonyl]amino]-phenyl]acetamide
N-Isopropyl-2-chloroacetanilide
N-Isopropyl-1-(3,5,5-trimethylcyclohexen-1-yl)-2-chloroacetamide
2',6'-Diethyl-N-(butoxymethyl)-2-chloroacetanilide
2',6'-Diethyl-N-(2-n-propoxyethyl)-2-chloroacetanilide
2',6'-Dimethyl-N-(1-pyrazol-1-ylmethyl)-2-chloroacetanilide
2',6'-Diethyl-N-methoxymethyl-2-chloroacetanilide
2'-Methyl-6'-ethyl-N-(2-methoxyprop-2-yl)-2-chloroacetanilide 2'-Methyl-6'-ethyl-N-(ethoxymethyl)-2-chloro-acetanilide
α,α,α-Trifluoro-2,6-dinitro-N,N-dipropyl-p-toluidine
N-(1,1-dimethylpropynyl)-3,5-dichlorobenzamide
Acids/Esters/Alcohols
2,2-Dichloropropionic acid
2-Methyl-4-chlorophenoxyacetic acid
2,4-Dichlorophenoxyacetic acid
Methyl-2-[4-(2,4-dichlorophenoxy)phenoxy]propionate
3-Amino-2,5-dichlorobenzoic acid
2-Methoxy-3,6-dichlorobenzoic acid
2,3,6-Trichlorophenylacetic acid
N-1-naphthylphthalamic acid
Sodium 5-[2-chloro-4-(trifluoromethyl)phenoxy]-2-nitrobenzoate
4,6-Dinitro-o-sec-butylphenol
N-(phosphonomethyl)glycine and its salts
Butyl (R)-2-[4-[(5-(trifluoromethyl)-2-pyridinyl) oxy]-phenoxy]propanoate
Ethers
2,4-Dichlorophenol-4-nitrophenyl ether
2-Chloro-α,α,α-trifluoro-p-tolyl-3-ethoxy-4-nitro-diphenyl ether
5-(2'chloro-4-trifluoromethylphenoxy)-N-methylsulfonyl-2-nitrobenazmide
1'-(Carboethoxy) ethyl 5-[2-chloro-4-(trifluoromethyl) phenoxy]-2-nitrobenzoate
Miscellaneous
2,6-Dichlorobenzonitrile
Monosodium acid methanearsonate
Disodium methanearsonate
2-(2-chlorophenyl)methyl-4,4-dimethyl-3-isoxazolidinone
7-Oxabicyclo (2.2.1) heptane, 1-methyl-4-(1-methylethyl)-2-(2-methylphenylmethoxy)-, exo-
Glufosinate and salts thereof
Glyphosate and salts thereof.

Fertilizers useful in combination with the active ingredients include, for example, ammonium nitrate, urea, potash and superphosphate. Other useful additaments include materials in which plant organisms take root and grow such as compost, manure, humus, sand and the like.

Herbicidal formulations of the types described above contemplated as within the purview of this invention are exemplified in illustrative embodiments below.

| I. Emulsifiable Concentrates | |
|---|---|
| | Weight Percent |
| Compound No. 8 | 11.60 |
| Aromatic 200 (Exxon, Houston, Texas): gamma butyrolactone (4:1) | 78.40 |
| Armul 1496 (Stepan, Winder, GA) | 5.00 |
| Armul 1505 (Stepan, Winder, GA | 5.00 |

| II. Suspension Concentrate | |
|---|---|
| | g/l |
| Compound No. 8 | 206.4 |
| Propylene glycol | 40.0 |
| Atlox 4913 (ICI, Wilmington, DE) | 20.0 |
| Atlox 4896 (ICI, Wilmington, DE) | 10.0 |
| Rhodorsil 432R (Rhône Poulenc, Paris, France) | 1.0 |
| Rhodopol 23 (Rhône Poulenc, Paris, France) | 2.0 |
| Phylatol (Coalite, Derbyshire, Great Britain) | 2.0 |
| Water (De-mineralised) | 805.5 |

When operating in accordance with the present invention, effective amounts of the compounds of this invention are applied to the soil containing the seeds, or vegetative propagules or may be incorporated into the soil media in any convenient fashion. The application of liquid and particulate solid compositions to the soil can be carried out by conventional methods, e.g., power duster, boom and hand sprayers and spray dusters. The compositions can also be applied from airplanes as a dust or a spray because of their effectiveness at low dosages. The exact amount of active ingredient to be employed is dependent upon various factors, including the plant species and stage of development thereof, the type and condition of soil, the amount of rainfall and the specific compounds employed. In elective pre-emergence application or to the soil, a dosage of from about 0.001 to about 11.2 kg/ha, preferably from about 0.01 to about 0.5 kg/ha, is usually employed. Lower or higher rates may be required in some instances. One skilled in the art can readily determine from this specification, including the above examples the optimum rate to be applied in any particular case.

The term "soil" is employed in its broadest sense to be-inclusive of all conventional "soils" as defined in *Webster's New International Dictionary*, Second Edition, Unabridged (1961). Thus, the term refers to any substance or medium in which vegetation may take root and grow, and includes not only earth but also compost, manure, muck, humus, loam, silt, mire, clay, sand and the like, adapted to support plant growth.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

We claim:

1. A compound according to Formula I:

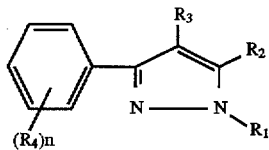

and agriculturally acceptable salts and hydrates thereof wherein $R_1$ is independently $C_{1-8}$ alkyl; $C_{3-8}$ cycloalkyl, cycloalkenyl, cycloalkylalkyl, or cycloalkylalkyl; $C_{2-8}$ alkenyl or alkynyl; benzyl; or said $R_1$ members substituted with halogen, amino, nitro, cyano, hydroxy, $C_{1-8}$ alkoxy, $C_{1-8}$ alkylthio, —C(=X)YR$_8$, —C(=X)R$_9$, YR$_{10}$, or NR$_{11}$R$_{12}$;

$R_2$ is $C_{1-6}$ haloalkyl;

$R_3$ is $C_{1-6}$ alkyl, $C_{1-6}$ haloalkyl, CHO or CH$_2$OH;

$R_4$ members are independently an $R_1$ member, $C_{1-8}$ thioalkyl, $C_{1-8}$ polyalkoxyalkyl, carbamyl, halogen, amino, nitro, cyano, hydroxy, $C_{6-2}$ aryl, aralkyl or alkaryl, —C(X)YR$_{13}$, —C(X)R$_{14}$, YR$_{15}$, or NR$_{16}$R$_{17}$ group; or two $R_4$ groups may be combined through a saturated and/or unsaturated carbon, or —(C=X)—, linkage to form a cyclic ring having up to 9 ring members which may be substituted with an $R_1$ member, halogen, amino, nitro, cyano, hydroxy, $C_{6-12}$ aryl, aralkyl, alkaryl, —C(=X)YR$_{13}$, —C(=X)R$_{14}$, YR$_{15}$ or NR$_{16}$R$_{17}$;

X is O, S(O)$_m$, NR$_{19}$ or CR$_{20}$R$_{21}$;

Y is O, S(O)$_m$ or NR$_{22}$; wherein at least one $R_4$ member is a non-halogen;

$R_{8-22}$ are hydrogen, $C_{1-8}$ alkyl, $C_{3-8}$ cycloalkyl, cycloalkenyl, cycloalkylalkyl, or cycloalkylalkyl, $C_{2-8}$ alkenyl or alkynyl, benzyl, or said $R_1$ members substituted with halogen, amino, nitro, cyano, hydroxy, $C_{1-8}$ alkoxy, $C_{1-8}$ alkylthio, $C_{6-2}$ aryl, aralkyl, alkaryl, carboxyl, alkoxy $C_{1-8}$-alkyl, $C_{1-8}$ alkylamino, di-$C_{1-8}$-alkylamino, $C_{1-8}$ alkoxy, or carbamyl;

m is 0–2 and n is 1–5.

2. A compounds according to claim 1 having formula

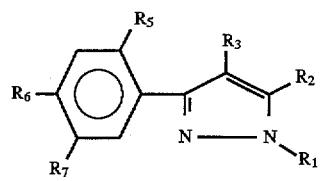

and agriculturally-acceptable salts and hydrates thereof wherein $R_1$ is $C_{1-6}$ alkyl;

$R_2$ is $C_{1-6}$ haloalkyl;

$R_3$ is $C_{1-6}$ alkyl, $C_{1-6}$ haloalkyl, CHO or CH$_2$OH;

$R_5$ and $R_6$ are independently halogen; and $R_7$ is an $R_1$ member,

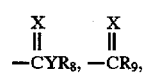

YR$_{10}$, or NR$_{11}$R$_{12}$.

3. A compound, salt and hydrate according to claim 2 wherein $R_1$ is CH$_3$;

$R_2$ is CF$_3$;

$R_3$ is CH$_3$, CH$_2$F or CF$_2$H;

$R_5$ is F;

$R_6$ is Cl; and $R_7$ is

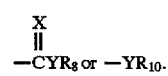

4. A compound according to claim 3 wherein said compounds are selected from the group consisting of 2-chloro-5-[1,4-dimethyl-5-(trifluoromethyl)-1H-pyrazol-3-yl]-4-fluorobenzoic acid, 1-methylethyl ester;

2-chloro-5-[1,4-dimethyl-5-(trifluoromethyl)-1H-pyrazol-3-yl]-4-fluorobenzoic acid ethyl ester;

2-chloro-5-[4-difluoromethyl)-1-methyl-5-(trifluoromethyl)-1H-pyrazol-3-yl]-4-fluorobenzoic acid, 1-methylethyl ester; and 2-chloro-4-fluoro-5-[4-(fluoromethyl)-1-methyl-5-(trifluoromethyl)-1H-pyrazol-3-yl]benzoic acid, 1-methylethyl ester.

5. Herbicidal composition comprising an adjuvant and a herbicidally-effective amount of a compound according to Formula I:

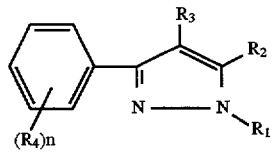

and agriculturally acceptable salts and hydrates thereof wherein

- $R_1$ is independently $C_{1-8}$ alkyl; $C_{3-8}$ cycloalkyl, cycloalkenyl, cycloalkylalkyl, or cycloalkenylalkyl; $C_{2-8}$ alkenyl or alkynyl; benzyl; or said $R_1$ members substituted with halogen, amino, nitro, cyano, hydroxy, $C_{1-8}$ alkoxy, $C_{1-8}$ alkylthio, —C(=X)YR$_8$, —C(=X)R$_9$, YR$_{10}$, or NR$_{11}$R$_{12}$;
- $R_{12}$ is $C_{1-6}$ haloalkyl;
- $R_3$ is $C_{1-6}$ alkyl, $C_{1-6}$ haloalkyl, CHO or CH$_2$OH;
- $R_4$ members are independently an $R_1$ member, $C_{1-8}$ thioalkyl, $C_{1-8}$ polyalkoxyalkyl, carbamyl, halogen, amino, nitro, cyano, hydroxy, $C_{6-12}$ aryl, aralkyl or alkaryl, —C(X)YR$_{13}$, —C(X)R$_{14}$, YR$_{15}$, or NR$_{16}$R$_{17}$ group; or two $R_4$ groups may be combined through a saturated and/or unsaturated carbon, or —(C=X)—, linkage to form a cyclic ring having up to 9 ring members which may be substituted with an $R_1$ member, halogen, amino, nitro, cyano, hydroxy, $C_{6-12}$ aryl, aralkyl, alkaryl, —C(=X)YR$_{13}$, —C(=X)R$_{14}$, YR$_{15}$ or NR$_{16}$R$_{17}$;
- X is O, S(O)$_m$, NR$_{19}$ or CR$_{20}$R$_{21}$;
- Y is O, S(O)$_m$ or NR$_{22}$; wherein at least one $R_4$ member is a non-halogen:
- $R_{8-22}$ are hydrogen, $C_{1-8}$ alkyl, $C_{3-8}$ cycloalkyl, cycloalkenyl, cycloalkylalkyl, or cycloalkenylalkyl, $C_{2-8}$ alkenyl or alkynyl, benzyl, or said $R_1$ members substituted with halogen, amino, nitro, cyano, hydroxy, $C_{1-8}$ alkoxy, $C_{1-8}$ alkylthio, $C_{6-12}$ aryl, aralkyl, alkaryl, carboxyl, alkoxy-$C_{1-8}$-alkyl, $C_{1-8}$ alkylamino, di-$C_{1-8}$-alkylamino, $C_{1-8}$ alkoxy, or carbamyl;
- m is 0–2 and
- n is 1–5.

6. Compositions according to claim 5 wherein the compound of Formula I is as in formula II:

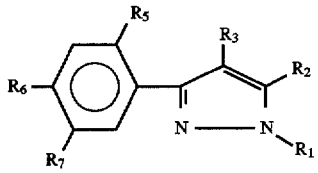

and agriculturally-acceptable salts and hydrates thereof wherein

- $R_1$ is $C_{1-6}$ alkyl;
- $R_2$ is $C_{1-6}$ haloalkyl;
- $R_3$ is $C_{1-6}$ alkyl, $C_{1-6}$ haloalkyl, CHO or CH$_2$OH;
- $R_5$ and $R_6$ are independently halogen; and
- $R_7$ is an $R_1$ member,

YR$_{10}$, or NR$_{11}$R$_{12}$.

7. Composition according to claim 6 where in Formula II

- $R_1$ is CH$_3$;
- $R_2$ is CF$_3$;
- $R_3$ is CH$_3$, CH$_2$F or CF$_2$H;
- $R_5$ is F;
- $R_6$ is Cl; and
- $R_7$ is

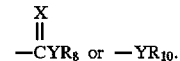

8. Composition according to claim 7 wherein said compounds is selected from the group consisting of

- 2-chloro-5-[1,4-dimethyl-5-(trifluoromethyl)-1H-pyrazol-3-yl ]-4-fluorobenzoic acid, 1-methylethyl ester;
- 2-chloro-5-[1,4-dimethyl-5-(trifluoromethyl)-1H-pyrazol-3-yl]-4-fluorobenzoic acid ethyl ester;
- 2-chloro-5-[4-difluoromethyl)-1-methyl-5-(trifluoromethyl)-1H-pyrazol-3-yl]-4-fluorobenzoic acid, 1-methylethyl ester; and
- 2-chloro-4-fluoro-5-[4-(fluoromethyl )-1-methyl-5-(trifluoromethyl)-1H-pyrazol-3-yl]benzoic acid, 1-methylethyl ester.

9. Method for combatting undesirable plants in crops comprising applying to the locus thereof a herbicidally-effective amount of a compound according to Formula I:

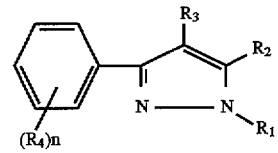

and agriculturally acceptable salts and hydrates thereof wherein

- $R_1$ is independently $C_{1-8}$ alkyl; $C_{3-8}$ cycloalkyl, cycloalkenyl, cycloalkylalkyl, or cycloalkenylalkyl; $C_{2-8}$ alkenyl or alkynyl; benzyl; or said $R_1$ members substituted with halogen, amino, nitro, cyano, hydroxy, $C_{1-8}$ alkoxy, $C_{1-8}$ alkylthio, —C(=X)YR$_8$, —C(=X)R$_9$, YR$_{10}$, or NR$_{11}$R$_{12}$;
- $R_2$ is $C_{1-6}$ haloalkyl;
- $R_3$ is $C_{1-6}$ alkyl, $C_{1-6}$ haloalkyl, CHO or CH$_2$OH;
- $R_4$ members are independently an $R_1$ member, $C_{1-8}$ thioalkyl, $C_{1-8}$ polyalkoxyalkyl, carbamyl, halogen, amino, nitro, cyano, hydroxy, $C_{6-12}$ aryl, aralkyl or alkaryl, —C(X)YR$_{13}$, —C(X)R$_{14}$, YR$_{15}$, or NR$_{16}$R$_{17}$ group; or two $R_4$ groups may be combined through a saturated and/or unsaturated carbon, or —(C=X)—, linkage to form a cyclic ring having up to 9 ring members which may be substituted with an $R_1$ member, halogen, amino, nitro, cyano, hydroxy, $C_{6-12}$ aryl, aralkyl, alkaryl, —C(=X)YR$_{13}$, —C(=X)R$_{14}$, YR$_{15}$ or NR$_{16}$R$_{17}$;
- X is O, S(O)$_m$, NR$_{19}$ or CR$_{20}$R$_{21}$;
- Y is O, S(O)$_m$ or NR$_{22}$; wherein at least one $R_4$ member is a non-halogen;
- $R_{8-22}$ are hydrogen, $C_{1-8}$ alkyl, $C_{3-8}$ cycloalkyl, cycloalkenyl, cycloalkylalkyl, or cycloalkenyl alkyl, $C_{2-8}$ alkenyl or alkynyl, benzyl, or said $R_1$ members substituted with halogen, amino, nitro, cyano, hydroxy, $C_{1-8}$ alkoxy, $C_{1-8}$ alkylthio, $C_{6-12}$ aryl, aralkyl, alkaryl, carboxyl, alkoxy-$C_{1-8}$-alkyl, $C_{1-8}$ alkylamino, di-$C_{1-8}$-alkylamino, $C_{1-8}$ alkoxy, or carbamyl;

m is 0–2 and n is 1–5.

10. Method according to claim 9 wherein the compounds of Formula I is compounds according to Formula II:

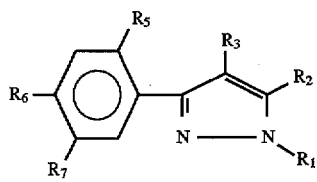

and agriculturally-acceptable salts and hydrates thereof wherein $R_1$ is $C_{1-6}$ alkyl;

$R_2$ is $C_{1-6}$ haloalkyl;

$R_3$ is $C_{1-6}$ alkyl, $C_{1-6}$ haloalkyl, CHO or $CH_2OH$;

$R_5$ and $R_6$ are independently halogen; and $R_7$ is an $R_1$ member,

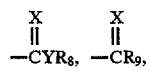

$YR_{10}$, or $NR_{11}R_{12}$.

11. Method according to claim 10 wherein in the compound, salt and hydrate of Formula II.

$R_1$ is $CH_3$;

$R_2$ is $CF_3$;

$R_3$ is $CH_3$, $CH_2F$ or $CF_2H$;

$R_5$ is F;

$R_6$ is Cl; and $R_7$ is

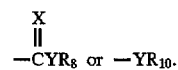

12. Method according to claim 11 wherein said compound is selected from the group consisting of 2-chloro-5-[1,4-dimethyl-5-(trifluoromethyl)-1H-pyrazol-3-yl]-4-fluorobenzoic acid, 1-methylethyl ester;

2-chloro-5-[1,4-dimethyl-5-(trifluoromethyl)-1H-pyrazol-3-yl]-4-fluorobenzoic acid ethyl ester;

2-chloro-5-[4-difluoromethyl)-1-methyl-5-(trifluoromethyl)-1H-pyrazol-3yl]-4-fluorobenzoic acid, 1-methylethyl ester; and 2-chloro-4-fluoro-5-[4-(fluoromethyl)-1-methyl-5-(trifluoromethyl)-1H-pyrazol-3-yl]benzoic acid, 1-methylethyl ester.

* * * * *

UNITED STATES PATENT AND TRADEMARK OFFICE
CERTIFICATE OF CORRECTION

PATENT NO. : 5,668,088
DATED : September 16, 1997
INVENTOR(S) : Bruce Hamper et al.

It is certified that error appears in the above-identified patent and that said Letters Patent is hereby corrected as shown below:

Column 46, line 5, delete "$C_{6-2}$" and insert --$C_{6-12}$--.

Column 46, line 11, delete "A compounds" and insert --A compound--.

Column 46, lines 11-12, after "having formula" insert --II:--.

Column 47, line 17, delete "$R_{12}$" and insert --$R_2$--.

Column 47, line 22, delete "$C_{62-12}$" and insert --$C_{6-12}$--.

Column 47, line 33, delete ":" and insert --;--.

Column 48, line 13, delete "compounds is" and insert --compound is--.

Column 49, line 4, delete "Formula I is compounds" and insert --Formula I is a compound--.

Column 50, line 16, delete "1-methylethyl 5 ester" and insert --1-methylethyl ester--.

Signed and Sealed this

Seventeenth Day of February, 1998

Attest:

BRUCE LEHMAN

Attesting Officer

Commissioner of Patents and Trademarks